US012788717B2

(12) United States Patent
Jermy et al.

(10) Patent No.: US 12,788,717 B2
(45) Date of Patent: Nov. 10, 2026

(54) MAGNETIC FERRITIC NANOCOMPOSITE

(71) Applicant: Imam Abdulrahman Bin Faisal University, Dammam (SA)

(72) Inventors: B. Rabindran Jermy, Dammam (SA); Vijaya Ravinayagam, Dammam (SA); Dana Abdulrahman Almohazey, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 174 days.

(21) Appl. No.: 18/926,415

(22) Filed: Oct. 25, 2024

(65) Prior Publication Data

US 2025/0049706 A1 Feb. 13, 2025

Related U.S. Application Data

(63) Continuation of application No. 17/375,079, filed on Jul. 14, 2021, now Pat. No. 12,161,756.

(51) Int. Cl.

| | |
|---|---|
| ***A61K 9/00*** | (2006.01) |
| ***A61K 31/573*** | (2006.01) |
| ***A61K 47/02*** | (2006.01) |
| ***A61K 47/10*** | (2017.01) |

(52) U.S. Cl.

CPC .......... *A61K 9/0092* (2013.01); *A61K 31/573* (2013.01); *A61K 47/02* (2013.01); *A61K 47/10* (2013.01)

(58) Field of Classification Search

CPC .... A61K 9/0092; A61K 31/573; A61K 47/02; A61K 47/10; A61K 9/5115; A61K 9/5146

See application file for complete search history.

(56) References Cited

U.S. PATENT DOCUMENTS

| | | | |
|---|---|---|---|
| 2007/0003753 | A1 | 1/2007 | Asgari |
| 2010/0233219 | A1 | 9/2010 | Aimi et al. |
| 2012/0294806 | A1 | 11/2012 | Chen et al. |
| 2020/0038525 | A1 | 2/2020 | Jermy et al. |
| 2020/0338122 | A1 | 10/2020 | Jermy et al. |

FOREIGN PATENT DOCUMENTS

| | | | |
|---|---|---|---|
| CN | 104225599 | B | 5/2017 |

OTHER PUBLICATIONS

Jermy, et al. ; Tuning pH sensitive chitosan and cisplatin over spinel ferrite/silica nanocomposite for anticancer activity in MCF-7 cell line; Journal of Drug Delivery Science and Technology, vol. 57; Jun. 2020; 3 Pages; Abstract Only.

Tarn, et al.; Mesoporous Silica Nanoparticle Nanocarriers—Biofunctionality and Biocompatibility; Acc Chem Res. Mar. 19, 2013: 46(3): 792-801; 20 Pages.

Yang, et al. ; Folic acid-functionalized magnetic $ZnFe_2O_4$ hollow microsphere core/mesoporous silica shell composite particles: Synthesis andapplication in drug release ; Materials Science and Engineering: C, vol. 33, Issue 5 ; Jul. 2013; 3 Pages ; Abstract Only.

Pindiprolu, et al.; Pulmonary delivery of nanostructured lipid carriers for effective repurposing of salinomycin as an antiviral agent; Medical Hypotheses; May 19, 2020; 8 Pages.

*Primary Examiner* — Robert A Wax
*Assistant Examiner* — Quanglong N Truong
(74) *Attorney, Agent, or Firm* — Oblon, McClelland, Maier & Neustadt, L.L.P.

(57) ABSTRACT

A nanocomposite comprising a nanocarrier, a pharmaceutical compound disposed on a surface of the nanocarrier, and a biocompatible coating disposed on the pharmaceutical compound. The nanocarrier comprises nanotubes of a silicate or aluminosilicate material, preferably halloysite, and nanoparticles of a magnetic transition metal ferrite material of formula $MFe_2O_4$, where M is selected from the group consisting of zinc, nickel, copper, manganese, and cobalt, the nanoparticles being disposed on an interior and/or an exterior surface of the nanotubes. The pharmaceutical compound is disposed in the pores and/or on the surface of the nanocarrier by a solution phase impregnation process. The nanomedicinal composition is used in a method of treating pulmonary infections. The nanomedicinal composition may be administered by inhalation.

14 Claims, 13 Drawing Sheets

MAGNETIC FERRITIC NANOCOMPOSITE

CROSS-REFERENCE TO RELATED APPLICATIONS

The present application is a Continuation of U.S. application Ser. No. 17/375,079, now allowed, having a filing date of Jul. 14, 2021.

BACKGROUND OF THE INVENTION

Field of the Invention

The present disclosure relates to a nanocomposite comprising a nanocarrier loaded with a pharmaceutical compound and covered with a biocompatible coating. The nanocomposite may be administered via inhalation for treating pulmonary infections.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Coronavirus disease (COVID-19) is caused by the severe acute respiratory syndrome corona virus 2 (SARS-COV-2). Pulmonary drug delivery systems have been developed to treat lung infections including COVID-19. The delivery of the drugs to a particular site, such as the pulmonary system, the main site for SARS-COV-2 invasion, is important as poor absorption and low bioavailability are observed with other delivery methods. Recently, many studies have shown promising results for pulmonary delivery of nanostructured carriers for delivery of antiviral agents. The most striking feature of such nanotherapeutics is the ability of a nanoparticle to accommodate several components into a single nano structure to generate multifunctional modality. Several nanocarriers based on liposomes, micelles, polymer conjugated with drugs and dendrimers has been reported for treating pulmonary infections. For a review of recent process in the field, see Pontes & Grenha [Pontes, J. F. & Grenha, A., Nanomaterials, 2020, 10, 2, 183].

Several antiviral drugs like dexamethasone, favipiravir, ribavirin, interferons, hydroxychloroquine combined with antibiotic azimethrone, lopinavir/ritonavir in combination with interferon, were found to be effective in treatment of COVID-19. However, dexamethasone may cause diabetes related complications, immune suppression, and hypertension in large doses. Poor gastrointestinal stability, low bioavailability, poor transport behavior, and side effects on other organs like kidney limit its therapeutic effectivity. The large doses required to overcome low bioavailability with conventional treatment methods in particular increase the risk for such side effects.

In view of the foregoing, an object of the present invention is to provide a nanocomposite comprising a nanocarrier loaded with a pharmaceutical compound and covered in a biocompatible coating that can be delivered via inhalation.

SUMMARY OF THE INVENTION

In one aspect the present disclosure relates to a nanocomposite, comprising a nanocarrier, a pharmaceutical compound disposed on a surface of the nanocarrier, and a biocompatible coating disposed on the pharmaceutical compound. The nanocarrier comprises nanotubes of a silicate or aluminosilicate material, and nanoparticles of a magnetic transition metal ferrite material of formula $MFe_2O_4$, where M is selected from the group consisting of zinc, nickel, copper, manganese, and cobalt, the nanoparticles being disposed on an interior and/or an exterior surface of the nanotubes.

In some embodiments, the nanotubes have an exterior surface which is negatively charged and an interior surface which is positively charged.

In some embodiments, the nanotubes have a mean nanotube outer diameter of 15 to 125 nm and a mean nanotube length of 0.25 to 7.5 μm.

In some embodiments, the nanotubes of a silicate or aluminosilicate material are halloysite.

In some embodiments, the nanoparticles have a mean particle size of 5 to 60 nm. In some embodiments, the nanoparticles are present in an amount of 1 to 50 wt %, based on a total weight of the nanocarrier.

In some embodiments, the nanocarrier has a surface area of 50 to 100 $m^2/g$, a pore volume of 0.2 to 0.4 $cm^3/g$, and a mean pore size of 10 to 20 nm.

In some embodiments, the pharmaceutical compound is dexamethasone.

In some embodiments, the pharmaceutical compound is present in an amount of 1 to 10 wt % based on a total weight of the nanocomposite.

In some embodiments, the biocompatible coating comprises polyethylene glycol.

In some embodiments, the polyethylene glycol has a number average molecular weight of 350 to 450 g/mol.

In some embodiments, the nanocomposite further comprises a targeting agent disposed on the surface of the nanocarrier and/or on the biocompatible coating.

In some embodiments, the nanocomposite has a surface area of 5 to 35 $m^2/g$ and a pore volume of 0.01 to 0.18 $cm^3/g$.

In some embodiments, the nanocomposite releases 1 to 30 mol % of the pharmaceutical compound after 50 to 250 hours at a pH of 4.5 to 7, based on an initial amount of pharmaceutical compound present in the nanocomposite.

The present disclosure also relates to a method of preparing the nanocomposite, the method comprising mixing an M source, an iron source, and the nanotubes of the silicate or aluminosilicate material in a first solvent to form a precursor mixture, adding a base to the precursor mixture to form a first reaction mixture, heating the reaction mixture to 75 to 105° C. to form a precipitate, isolating the precipitate to form a first product, calcining the first product to form the nanocarrier, mixing the nanocarrier and the pharmaceutical compound in a second solvent form a loaded nanocarrier, mixing the loaded nanocarrier and the biocompatible coating in a third solvent form a coated nanocarrier, and lyophilizing the coated nanocarrier to form the nanocomposite.

In some embodiments, the silicate or aluminosilicate material is halloysite.

In some embodiments, the pharmaceutical compound is dexamethasone and the second solvent comprises phosphate buffered saline and methanol.

In some embodiments, the biocompatible coating is polyethylene glycol and the third solvent is water.

The present disclosure also relates to a method of treating a pulmonary infection, the method comprising administering by inhalation a pharmaceutical composition comprising the nanocomposite.

In some embodiments, the pharmaceutical compound is dexamethasone and the nanocomposite is administered in an amount of 0.5 to 15 μg/mL of infected tissue.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 3A shows the region 400 to 1800 $cm^{-1}$ and FIG. 3B shows the region 2000 to 4000 $cm^{-1}$;

FIG. 6A is an elemental mapping showing the distribution of elements, FIG. 6B shows an elemental map of carbon, FIG. 6C shows an elemental map of oxygen, FIG. 6D shows an elemental map of silicon, FIG. 6E shows an elemental map of aluminum, FIG. 6F shows an elemental map of iron, FIG. 6G shows an elemental map of zinc, and FIG. 6H shows an EDS spectra of the area depicted in FIGS. 6A-6G and the elemental composition of said area;

FIG. 7A is for $ZnFe_2O_4$/Halloysite, FIG. 7B is for $NiFe_2O_4$/Halloysite, and FIG. 7C shows both $ZnFe_2O_4$/Halloysite and $NiFe_2O_4$/Halloysite with and without PEG coating;

FIG. 8A is for $ZnFe_2O_4$-containing nanocomposites, and FIG. 8B is for $NiFe_2O_4$-containing nanocomposites;

FIG. 9A is for cells treated at 0.075 mg/mL, FIG. 9B is for cells treated at 0.15 mg/mL, and FIG. 9C is for cells treated at 0.3 mg/mL

DETAILED DESCRIPTION OF THE INVENTION

Figure 1:
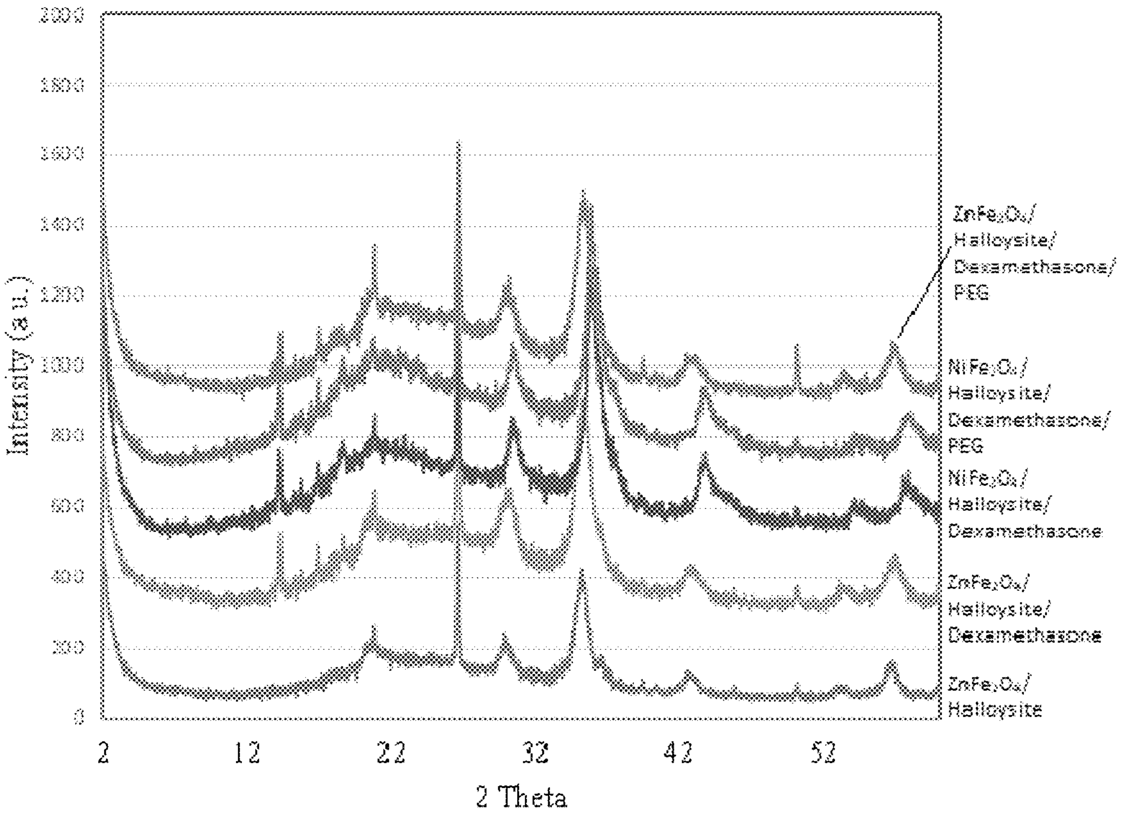
FIG. 1 shows X-ray diffraction patterns of various nanocomposites of the current invention including Zinc ferrite/Halloysite, Zinc ferrite/Halloysite/Dexamethasone, Nickel ferrite/Halloysite/Dexamethasone, Nickel ferrite/Halloysite/Dexamethasone/PEG and Zinc ferrite/Halloysite/Dexamethasone/PEG.

In the following description, it is understood that other embodiments may be utilized and structural and operational changes may be made without departure from the scope of the present embodiments disclosed herein.

Definitions

As used herein the words "a" and "an" and the like carry the meaning of "one or more."

As used herein, the terms "optional" or "optionally" means that the subsequently described event(s) can or cannot occur or the subsequently described component(s) may or may not be present (e.g., 0 wt. %).

Nanocomposite

According to a first aspect, the present disclosure relates to a nanocomposite, comprising a nanocarrier, a pharmaceutical compound disposed on a surface of the nanocarrier, and a biocompatible coating disposed on the pharmaceutical compound. The nanocarrier comprises nanotubes of a silicate or aluminosilicate material, and nanoparticles of a magnetic transition metal ferrite material of formula $MFe_2O_4$, where M is selected from the group consisting of zinc, nickel, copper, manganese, and cobalt, the nanoparticles being disposed on an interior and/or an exterior surface of the nanotubes.

In general, the nanotubes may be made up of any suitable silicate or aluminosilicate material known to one of ordinary skill in the art. Aluminate materials which do not contain silicon, such as alumina nanotubes, however, are not contemplated to be used in the invention in any embodiments.

Aluminosilicate materials may be characterized by a ratio of Si to Al present in the material. In general, the aluminosilicate material may have any suitable Si:Al molar ratio. Examples of such suitable Si:Al molar ratios are 1000:1 to 1:250, preferably 500:1 to 1:200, preferably 250:1 to 1:100, preferably 150:1 to 1:75, preferably 100:1 to 1:50, preferably 50:1 to 1:25, preferably 25:1 to 1:10, preferably 10:1 to 1:5, preferably 5:1 to 1:2.5, preferably 2.5:1 to 1:1.5, preferably 1.5:1 to 1:1. In general, the elemental composition of the silicate or aluminosilicate material, including the Si:Al molar ratio, may be determined by any suitable technique known to one of ordinary skill in the art. Examples of suitable such techniques include mass spectrometry techniques such as inductively-coupled plasma mass spectrometry (ICP-MS), atomic emission spectroscopy techniques such as inductively-coupled plasma atomic emission spectroscopy (ICP-AES) (also referred to as ICP optical emission spectroscopy, ICP-OES), atomic absorption spectroscopy techniques such as inductively-coupled plasma atomic absorption spectroscopy (ICP-AAS), and X-ray spectroscopy techniques such as X-ray photoelectron spectroscopy.

Silicates and aluminosilicates are materials which comprise $SiO_4$ tetrahedra (and $AlO_4^-$ tetrahedra, $AlO_6$ octahedra, and/or $Al(OH)_6$ octahedra in the case of aluminosilicates) joined together in a wide variety of structural motifs. The tetrahedra (and if applicable octahedra) in the silicate or aluminosilicate material of the present invention may in general adopt any structural motif present in other silicate materials, such as isolated tetradhedra as in neosilicates (single tetrahedra, also called orthosilicates) and sorosilicates (double tetrahedra), chains of tetrahedra such as inosilicates (both single chain as in pyroxene group silicates and double chain as in amphibole group silicates), rings of tetrahedra as in cyclosilicates, sheets of tetrahedra as in phyllosilicates, and three-dimensional frameworks as in tectosilicates. In some aluminosilicates, the material comprises a substructure comprising silicon-containing and/or aluminum-containing tetrahedral and a substructure comprising aluminum-containing octahedral. An example of such an arrangement is the mineral kaolin, which comprises sheets of alternating tetrahedra-containing layers and octahedra-containing layers. The arrangement of isolated tetrahedra, chains of tetrahedra, sheets of tetrahedra, or three-dimensional frameworks may give rise to channels, pores, cages, or other spaces within the silicate or aluminosilicate which is capable of hosting material which is not the silicate or aluminosilicate itself. Examples of materials, particularly those relevant to the current disclosure, include water, organic molecules, and inorganic nanoparticles. While the larger structures formed of tetrahedra (i.e. chains, rings, sheets, and three-dimensional frameworks) may themselves be ordered, the arrangement of these larger structures may be disordered. Such disorder may give rise to a material which is amorphous by techniques for determining crystallinity or crystal structure such as powder X-ray diffraction (PXRD). Alternatively, the larger structures may be ordered, giving rise to a crystalline material.

In preferred embodiments, the nanotubes of a silicate or aluminosilicate material comprise sheets of tetrahedra and optionally octahedra. Such sheets may be similar to those found in phyllosilicate materials. Preferably, such sheets form the shape of the nanotubes by rolling or scrolling to form a cylindrical shape having an interior void which is accessible by open ends of the cylinder. In such a configuration, the edges of the sheet or sheets which are rolled may be joined together to form a smooth tube shape or may be non-joined. Such a non-joined configuration may be described as a scroll shape having a cross-sectional shape similar to a spiral. In such non-joined configurations, a portion of the nanotube may comprise a region in which the sheet overlaps itself. In general, there is no limit to the number of times a sheet may overlap itself in the non-joined configuration.

The size and shape of nanotubes are typically defined by a nanotube outer diameter, a nanotube length, and sometimes an aspect ratio. Sometimes an inner diameter or a nanotube wall thickness is also used to further define the size and shape of nanotubes. In some embodiments, the nanotubes have a mean nanotube outer diameter of 10 to 125 nm, preferably 12.5 to 110 nm, preferably 15 to 100 nm, preferably 17.5 to 95 nm, preferably 20 to 90 nm, preferably 22.5 to 85 nm, preferably 25 to 80 nm, preferably 27.5 to 75 nm, preferably 30 to 70 nm. In some embodiments, the nanotubes have a mean inner diameter of 5 to 22.5 nm, preferably 7.5 to 20 nm, preferably 10 to 17.5 nm, preferably 11 to 16 nm, preferably 12 to 15 nm. In some embodiments, the nanotubes have a mean nanotube length of 0.25 to 7.5 μm, preferably 0.35 to 7 μm, preferably 0.5 to 5 μm preferably 0.75 to 4 μm, preferably 0.9 to 3.5 μm, preferably 1 to 3 μm. In some embodiments, the nanotubes have an aspect ratio of 2:1 to 750:1, preferably 5:1 to 500:1, preferably 7.5:1 to 250:1, preferably 10:1 to 150:1, preferably 12.5:1 to 125:1, preferably 14:1 to 100:1.

The shape of the nanotubes, being hollow, gives the nanotubes an interior surface and an exterior surface. In some embodiments, the interior surface is substantially the same as the exterior surface. In this context, "substantially the same" may refer to or be measured by any suitable structural or functional parameter or property known to one of ordinary skill in the art. Examples of such suitable structural parameters or properties include, but are not limited to chemical composition (including in particular Si:Al molar ratio), charge identity or density, orientation of tetrahedra, porosity, crystallographic characteristic such as strain or orientation, functional group identity or density, and binding or adsorption affinity for organic molecules and/or inorganic materials. In alternative embodiments, the interior surface is not substantially the same as the exterior surface. In some embodiments, the nanotubes have an exterior surface which is negatively charged and an interior surface which is positively charged. In some embodiments, such a charge difference is the result of a compositional difference between the exterior surface and the interior surface. Such a compositional difference may be in the form of a difference in an amount of silicon and/or aluminum present. In some embodiments, the exterior surface is silicon-rich (e.g. having a Si:Al molar ratio of approximately 1000:1 to 5:1). In some embodiments, the interior surface is aluminum-rich (e.g. having a Si:Al molar ratio of 1:2.5 to 1:250).

The shape of the nanotubes encloses an interior volume bound by the interior surface of the nanotube. The interior volume may be substantially cylindrical in shape. The nanotubes have at least one (preferably both) ends open, permitting substances to pass into the interior volume through said open ends. Materials (e.g. the nanoparticles) may be contained within the interior volume. Such materials may remain within the interior volume though interaction with the interior surface of the nanotube. In some embodiments, the layers of the silicate or aluminosilicate material may further comprise in-layer pores. Such in-layer pores are preferably oriented substantially perpendicular to the length of the nanotube. The in-layers pores may allow access to the interior volume or to an interlayer volume described below. Such pores may comprise a pore wall. This pore wall is a distinct surface from the interior surface and the exterior surface of the nanotube. The pore wall may be substantially the same as one or both of the interior surface and the exterior surface of the nanotube. Alternatively, the pore wall may be distinct from the interior surface or the exterior surface in terms of properties such as chemical composition (including in particular Si:Al molar ratio), charge identity or density, orientation of tetrahedra, crystallographic characteristic such as strain or orientation, functional group identity or density, and binding or adsorption affinity for organic molecules and/or inorganic materials. Embodiments in which the nanotubes comprise more than one layer of silicate or aluminosilicate material, the nanotubes may further comprise an interlayer volume defined between the layers. The interlayer volume may be defined by an inner interlayer surface and an outer interlayer surface. Due to the orientation, the inner interlayer surface may be substantially the same as the exterior surface of the nanotube while the outer interlayer surface may be substantially the same as the interiors surface of the nanotube. The interlayer volume may be accessible at the open ends of the nanotubes or by in-layer pores described above.

In preferred embodiments, the nanotubes of a silicate or aluminosilicate material are halloysite. Halloysite is a naturally occurring clay material comprising nanotubes made of aluminosilicate kaolin sheets rolled into a tube shape. Sometimes the kaolin sheets are rolled several times. As described above, such kaolin sheets comprise a tetrahedral layer comprising silicon-containing tetrahedra and an octahedral layer comprising aluminum-containing octahedral. These sheets are typically rolled to place the tetrahedral layer on the exterior surface of the nanotube and the octahedral layer on the interior surface of the nanotube. The silicon-rich tetrahedral layer gives the nanotube an exterior surface rich in siloxane functional groups and typically a negative charge. The aluminum-rich octahedral layer gives the nanotube an interior surface rich in aluminol functional groups and typically a positive charge.

In some embodiments, the nanotubes are surface modified prior to use in the nanocarrier. Such surface modifications may change the surface properties of the nanotubes, for example by increasing or decreasing the number or concentration of functional groups found on unmodified nanotubes or by introducing new functional groups to the nanotubes. Examples of such new functional groups include, but are not limited to carboxylic acid or carboxylate groups, amine or ammonium groups, sulfo groups, and phosphate groups. Such functional groups may be charged or uncharged. In some embodiments, the surface modification changes the surface charge of the interior surface, the exterior surface, or both of the modified nanotubes compared to unmodified nanotubes. Preferably, the surface modification does not change the surface charge of the interior surface, exterior surface, or both of the modified nanotubes compared to unmodified nanotubes. Such surface modification may be performed using any suitable method or with any suitable surface modifying agent or agents known to one of ordinary skill in the art. One example of such a method is the use of silanes or organosilicates bearing one or more functional groups to be added by the surface modification. Such surface modification may result in said functional groups being attached to the nanotubes by covalent bonds. Alternatively, said functional groups may be attached to the nanotubes by a non-covalent interaction, for example electrostatic interaction, physisorption, or hydrogen bonding. For an example of such surface modification particularly relevant to embodiments of the current invention which use halloysite nanotubes, see U.S. published application 20190270646A1. In some embodiments, the surface modifying agent(s) are substantially free of silianes. In some embodiments, the surface modifying agent(s) are substantially free of organosilicates. In some embodiments, the surface modifying agent(s) are substantially free of amino acids. In some embodiments, the surface modifying agent(s) are substantially free of short peptides (i.e. 2-20 residues). In some embodiments, the surface modifying agent(s) are substantially free of chromium salts (chrome alum, chromium acetate, etc.); calcium salts (calcium chloride, calcium hydroxide, etc.); aluminum salts (aluminum chloride, aluminumhydroxide, etc.); dialdehydes (glutaraldehyde, etc.); carbodiimides (EDC, WSC, N-hydroxy-5-norbomene-2,3-di-carboxylmide (HONB), N-hydroxysuccinic acid imide (HOSu), dicyclohexylcarbodiimide (DCC), etc.); N-hydroxysuccinimide; and/or phosphorus oxychloride. In some embodiments, the surface modifying agent(s) are substantially free of proteins. Examples of such proteins include, but are not limited to collagen, gelatin, albumin, ovalbumin, casein, transferrin, fibrin, and fibrinogen.

The nanocarrier also comprises nanoparticles of a magnetic transition metal ferrite material of formula $MFe_2O_4$, where M is selected from the group consisting of zinc, nickel, copper, manganese, and cobalt, the nanoparticles being disposed on an interior and/or an exterior surface of the nanotubes. Nanoparticles which are disposed on an interior surface of the nanotubes may be within the interior volume described above. In preferred embodiments, M is selected from the group consisting of zinc and nickel. In some embodiments, the magnetic transition metal ferrite nanoparticles are crystalline by PXRD. In some embodiments, the magnetic transition metal ferrite material crystallizes in the spinel crystal structure. The spinel crystal structure is characterized by a cubic close packed lattice of anions (in this case oxygen anions), in which the cations (M and Fe) occupy some or all of the tetrahedral sites and octahedral sites. In the normal spinel structure, divalent cations occupy tetrahedral holes and trivalent cations occupy octahedral holes. In the inverse spinel structure, the divalent cations occupy octahedral holes while half of the trivalent cations occupy octahedral holes, and the other half of the trivalent cations occupy tetrahedral holes. Intermediate structures between these end members with different cation ordering schemes also exist, including random cation distribution (also known as cation disordered structures). In some embodiments, the magnetic transition metal ferrite material crystallizes in the normal spinel structure. In alternative embodiments, the magnetic transition metal ferrite material crystallizes in the inverse spinel structure. In other alternative embodiments, the magnetic transition metal ferrite material crystallizes in an intermediate spinel structure. In alternative embodiments, the magnetic transition metal ferrite nanoparticles are not crystalline by PXRD.

In general, the magnetic transition metal ferrite material nanoparticles can be any shape known to one of ordinary skill in the art. Examples of suitable shapes the magnetic transition metal ferrite material nanoparticles may take include spheres, spheroids, lentoids, ovoids, solid polyhedra such as tetrahedra, cubes, octahedra, icosahedra, dodecahedra, rectangular prisms, triangular prisms (also known as nanotriangles), nanoplatelets, nanodisks, blocks, flakes, discs, granules, angular chunks, and mixtures thereof. Nanorods or nanowires are not a shape that the magnetic transition metal ferrite material nanoparticles are envisioned as having in any embodiments.

In some embodiments, the magnetic transition metal ferrite material nanoparticles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of magnetic transition metal ferrite material nanoparticles having a different shape. As used herein, the term "non-uniform shape" refers to an average consistent shape that differs by more than 10% of the distribution of magnetic transition metal ferrite material nanoparticles having a different shape. In one embodiment, the shape is uniform and at least 90% of the magnetic transition metal ferrite material nanoparticles are spherical or substantially circular, and less than 10% are polygonal. In another embodiment, the shape is non-uniform and less than 90% of the magnetic transition metal ferrite material nanoparticles are spherical or substantially circular, and greater than 10% are polygonal.

In some embodiments, the magnetic transition metal ferrite material nanoparticles have a mean particle size of 1 to 100 nm, preferably 2.5 to 75 nm, preferably 5 to 60 nm. In embodiments where the magnetic transition metal ferrite material nanoparticles are spherical, the particle size may refer to a particle diameter. In embodiments where the magnetic transition metal ferrite material nanoparticles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass.

In some embodiments, the magnetic transition metal ferrite material nanoparticles are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 10%, preferably less than 8%, preferably less than 6%, preferably less than 5%, preferably less than 4%, preferably less than 3%, preferably less than 2%. In some embodiments, the magnetic transition metal ferrite material nanoparticles of the present disclosure are monodisperse having a particle size distribution ranging from 80% of the average particle size to 120% of the average particle size, preferably 90-110%, preferably 95-105% of the average particle size. In some embodiments, the magnetic transition metal ferrite material nanoparticles are not monodisperse.

In some embodiments, the magnetic transition metal ferrite material nanoparticles are present in an amount of 1 to 50 wt %, preferably 5 to 47.5 wt %, preferably 10 to 45 wt %, preferably 12.5 to 42.5 wt %, preferably 15 to 40 wt %, preferably 17.5 to 37.5 wt %, preferably 20 to 35 wt %, preferably 22.5 to 32.5 wt %, preferably 24 to 31 wt %, preferably 25 to 30 wt %, based on a total weight of the nanocarrier.

In some embodiments, the nanocarrier has a surface area of 50 to 100 $m^2/g$, preferably 52.5 to 97.5 $m^2/g$, preferably 55 to 95 $m^2/g$, preferably 57.5 to 92.5 $m^2/g$, preferably 60 to 90 $m^2/g$, preferably 62.5 to 87.5 $m^2/g$, preferably 65 to 85 $m^2/g$, preferably 67.5 to 82.5 $m^2/g$, preferably 70 to 80 $m^2/g$, preferably 72.5 to 77.5 $m^2/g$, preferably 74 to 76 $m^2/g$. In some embodiments, the nanorcarrier has a pore volume of 0.2 to 0.4 $cm^3/g$, preferably 0.21 to 0.35 $cm^3/g$, preferably 0.22 to 0.325 $cm^3/g$, preferably 0.23 to 0.30 $cm^3/g$, preferably 0.24 to 0.29 $cm^3/g$, preferably 0.25 to 0.28 $cm^3/g$, preferably 0.26 to 0.27 $cm^3/g$, preferably 0.27 $cm^3/g$. In some embodiments, the nanocarrier has a mean pore size of 10 to 20 nm, preferably 10.5 to 19 nm, preferably 11 to 18 nm, preferably 11.5 to 17 nm, preferably 12 to 16 nm, preferably 12.5 to 15 nm, preferably 13 to 15 nm, preferably 13.5 to 14.5 nm, preferably 14 nm. The surface area, pore volume, and pore size ranges listed here refer to the nanocarrier alone (i.e. without the pharmaceutical compound and/or biocompatible coating.

In some embodiments, the nanocarrier is surface modified prior to use in the nanocomposite. Such surface modifications may change the surface properties of the nanotubes and/or the nanoparticles, as described above. In some embodiments, the nanocarrier is subjected to a surface modification which modifies the surface of the nanoparticles but does not modify one or both surfaces of the nanotubes. In some embodiments, the nanocarrier is subjected to a surface modification which modifies one or both surfaces of the nanotubes but does not modify the surface of the nanoparticles. In some embodiments, the surface modification of the nanocarrier is substantially the same as the surface modification of the nanotubes. In alternative embodiments, the surface modification of the nanocarrier is not substantially the same as the surface modification of the nanotubes.

The nanocarrier is loaded with a pharmaceutical compound. This pharmaceutical compound is disposed on a surface of the nanocarrier. This surface may include an interior surface of the nanotube, an exterior surface of the nanotube, a pore wall surface of the nanotube, and/or a surface of the nanoparticles. Such a surface should be understood to include modified surfaces as described above. In some embodiments, the pharmaceutical compound may interact with the surface of the nanocarrier via any suitable interaction known to one of ordinary skill in the art. Such interactions may be, for example physisorption (e.g. Van der Waals interactions), ion-ion interactions, ion-dipole interactions, dipole-dipole interactions, and hydrogen bonding. Such interaction may be through or involving appropriate functional groups on the pharmaceutical compound. Examples of such functional groups include, but are not limited to oxygen-containing functional groups such as alcohols, alkoxides, carboxylic acids and carboxylates, esters, ketones, and ethers; nitrogen-containing functional groups such as amines, amides, azides, diimides, imines, porphyrins, imides, isonitriles, nitriles, and nitro functional groups; phosphorous-containing functional groups such as phosphines, phosphites, phosphates, phosphonites, phosphonates, phosphinites, and phosphinates; and sulfur-containing functional groups such as thiols, thiolates, disulfides, sulfones, sulfonic acids and sulfonates, sulfoxides, thials, thioesters, thiosulfinates, thiocarboxylic acids and thiocarboxylates, sulfinic acids and sulfinates, thiocyanates, and isothiocyanates. The pharmaceutical compound may be electrically neutral or may have a charge, the charge being either positive or negative. A pharmaceutical compound which is electrically neural may be devoid of charges or may have a combination of positive and negative charges in equal number so as to balance to electrically neutral (e.g. zwitterionic). A pharmaceutical compound which is electrically neutral may interact to an equal extent with or be disposed equally upon both the interior and exterior surfaces of the nanocarrier. Alternatively, a pharmaceutical compound which is electrically neutral may preferentially interact with either the interior or exterior surface of the nanocarrier. A pharmaceutical compound which bears a positive charge may preferentially interact with or be disposed upon the exterior surface of the nanocarrier which bears a negative charge. A pharmaceutical compound which bears a negative charge may preferentially interact with or be disposed upon the interior surface of the nanocarrier which bears a positive charge.

In some embodiments, the pharmaceutical compound is a steroid. In some embodiments, the pharmaceutical is a corticosteroid. In some embodiments, the pharmaceutical compound is a glucocorticoid. In some embodiments, the pharmaceutical compound is dexamethasone.

In some embodiments, the pharmaceutical compound is present in an amount of 1 to 10 wt %, preferably 1.5 to 9.5 wt %, preferably 2 to 9 wt %, preferably 2.5 to 8.5 wt %, preferably 3 to 8 wt %, preferably 3.5 to 7.5 wt %, preferably 4 to 7 wt %, preferably 4.25 to 6.5 wt %, preferably 4.5 to 6 wt %, preferably 4.75 to 5.5 wt %, preferably 5 wt %, based on a total weight of the nanocomposite.

The nanocomposite further comprises a biocompatible coating disposed on the pharmaceutical compound. In general, the biocompatible coating may be any suitable coating known to one of ordinary skill in the art which is appropriate for use in biomedical applications. Examples of such suitable biocompatible coatings include, but are not limited to, agarose, agar, carrageen, alginic acid, alginate, an alginic acid derivative, hyaluronic acid or a hyaluronate derivative, a polyanionic polysaccharide, chitin, chitosan, fibrin, pectin, collagen, fibronectin, a polyglycolide, a polylactide, a polycaprolactone, a dextran or copolymer thereof, polyvinyl pyrrolidone, a polyacrylate, a wax, wool fat, poly(L-lactic acid), poly(DL-Lactic acid), copoly(lactic/glycolic acid), cellulose, a cellulose derivative, a glycol, a polyglycol, polylactide-polyglycolide, polymethyldisiloxane, polycaprolactone, polylactic acid, and ethylene vinyl acetate. In some embodiments, the nanocomposite is substantially free of polyvinyl alcohol. In some embodiments, the nanocomposite is substantially free of poly(ethylene oxide)-poly (propylene oxide)-poly(ethylene oxide) triblock copolymer (PEO-PPO-PEO polymer). Such PEO-PPO-PEO block copolymers are also known as a Pluronic, for example Pluronic F68 and Pluronic F127. In some embodiments, the nanocomposite is substantially free of poly(N-isopropyl acrylamide). In some embodiments, the nanocomposite is substantially free of proteins. Examples of such proteins include, but are not limited to collagen, gelatin, albumin, ovalbumin, casein, transferrin, fibrin, and fibrinogen. In some embodiments, the biocompatible coating acts to prevent the release of the pharmaceutical compound from the nanocomposite. Such prevention may be a result of mechanical interaction (e.g. physically blocking desorption or other release mechanism), chemical interaction, or both. In some embodiments, the biocompatible coating is capable of being degraded or removed from the nanocomposite by a natural action or biological process which may be present in a tissue or subject. Such removal or degradation may be useful in facilitating release of the pharmaceutical compound from the nanocomposite. In some embodiments, the biocompatible coating comprises polyethylene glycol. In some embodiments, the polyethylene glycol has a number average molecular weight of 350 to 450 g/mol, preferably 360 to 440 g/mol, preferably 370 to 430 g/mol, preferably 375 to 425 g/mol, preferably 380 to 420 g/mol, preferably 385 to 415 g/mol, preferably 390 to 410 g/mol, preferably 395 to 405 g/mol, preferably 400 g/mol. In some embodiments, the biocompatible coating is present in the nanocomposite in an amount of 40 to 85 wt %, preferably 45 to 82.5 wt %, preferably 50 to 80 preferably 55 to 77.5 wt %, preferably 60 to 75 wt %, preferably 62.5 to 72.5 wt %, preferably 65 to 70 wt %, preferably 66 to 67 wt %, based on a total weight of the nanocomposite.

In some embodiments, the nanocomposite further comprises a targeting agent disposed on the surface of the nanocarrier and/or on the biocompatible coating. The targeting agent may be useful for facilitating, causing, enhancing, or otherwise affecting interaction of the nanocomposite with an organ, tissue, or cell type. In some embodiments, the targeting agent interacts with cell surface moieties which are present on a cellular surface of a particular cell or cell type. For example, the targeting agent may interact with moieties which are present to a greater degree, for example in number, density, or both, on one type of cell compared to another type of cell. In general, the targeting agent may be any suitable targeting agent known to one of ordinary skill in the art. Examples of such targeting agents include, but are not limited to antibodies, synthetic molecular imprint systems, DNA, RNA, proteins, lipids, cell-surface receptors, peptides, saccharides, aptamers, glycoproteins, glycosides, small molecules, and pharmaceutical agents. In some embodiments, the targeting agent is angiotensin. In some embodiments, the targeting agent preferentially interacts with an angiotensin-converting enzyme. In some embodiments, the targeting agent preferentially interacts with angiotensin-converting enzyme 2. In alternative embodiments, the targeting agent is angiotensin-converting enzyme 2.

In general, the targeting agent may be disposed upon the surface of the nanocarrier and/or on the biocompatible coating through any suitable interaction known to one of ordinary skill in the art. Examples of such interactions include, but are not limited to covalent bonds, van der Waals interactions, physisorption, chemisorption, electrostatic interactions, protein-protein interactions, enzyme-substrate interactions, antibody-antigen interactions, or combinations thereof. In general, the targeting agent may be disposed upon the surface of the nanocarrier and/or on the biocompatible coating using any suitable technique known to one of ordinary skill in the art. See, for example, Yoo, et. al. [Yoo, J., et. al., Cancers (Basel), 2019, 11, 5, 640, incorporated herein by reference in its entirety].

In some embodiments, the targeting agent facilitates endosomal delivery of the nanocomposite.

The incorporation of the pharmaceutical compound and the biocompatible coating gives the nanocomposite different properties, particularly those related to surface structure and/or porosity. Such changes may be attributed to the presence of the pharmaceutical compound and the biocompatible coating on an interior, exterior, and/or pore wall surface of the nanocarrier. In some embodiments, the nanocomposite has a surface area of 5 to 35 $m^2/g$, preferably 7.5 to 30 $m^2/g$, preferably 10 to 27.5 $m^2/g$, preferably 12.5 to 25 $m^2/g$, preferably 13 to 22.5 $m^2/g$, preferably 14 to 20 $m^2/g$, preferably 15 to 19 $m^2/g$, preferably 16 to 18 $m^2/g$, preferably 17 $m^2/g$. In some embodiments, the nanocomposite has a pore volume of 0.01 to 0.18 $cm^3/g$, preferably 0.02 to 0.16 $cm^3/g$, preferably 0.03 to 0.15 $cm^3/g$, preferably 0.04 to 0.14 $cm^3/g$, preferably 0.05 to 0.13 $cm^3/g$, preferably 0.06 to 0.12 $cm^3/g$, preferably 0.07 to 0.11 $cm^3/g$, preferably 0.08 to 0.10 $cm^3/g$, preferably 0.09 $cm^3/g$. In some embodiments, the nanocomposite has a mean pore size of 15 to 30 nm, preferably 16 to 28 nm, preferably 17 to 26 nm, preferably 18 to 24 nm, preferably 19 to 22 nm, preferably 20 to 21 nm. In some embodiments, the nanocomposite has a saturation magnetization of 0.01 to 1 emu/g, preferably 0.05 to 0.75 emu/g, preferably 0.075 to 0.5 emu/g, preferably 0.09 to 0.4 emu/g, preferably 0.1 to 0.3 emu/g, preferably 0.125 to 0.275 emu/g, preferably 0.15 to 0.25 emu/g, preferably 0.175 to 0.225 emu/g, preferably about 0.2 emu/g.

In some embodiments, the nanocomposite releases 1 to 30 mol %, preferably 2.5 to 25 mol %, preferably 5 to 15 mol %, preferably 7.5 to 10 mol % of the pharmaceutical compound after 50 to 250 hours, preferably 75 to 225 hours, preferably 100 to 200 hours, preferably 125 to 175 hours, preferably 150 hours at a pH of 4.5 to 7, preferably 4.75 to 6.75, preferably 5 to 6.5, preferably 5.25 to 6, preferably 5.5 to 5.75 based on an initial amount of pharmaceutical compound present in the nanocomposite. In some embodiments, the nanocomposite releases less than 10 mol %, preferably less than 9 mol %, preferably less than 8 mol %, preferably less than 7 mol %, preferably less than 6 mol %, preferably less than 5 mol % of the pharmaceutical compound after 50 to 250 hours, preferably 75 to 225 hours, preferably 100 to 200 hours, preferably 125 to 175 hours, preferably 150 hours at a pH of at least 7.1, preferably at least 7.2, preferably at least 7.3, preferably at least 7.4. Such a difference in the release rate and/or total amount of pharmaceutical compound released from the nanocomposite may be advantageous for selective delivery of the pharmaceutical compound.

The pH-sensitive release of the pharmaceutical compound may be advantageous for targeted delivery of the pharmaceutical compound to a specific organ, tissue, or cell type. In some embodiments, the nanocomposite is delivered to a target cell and is incorporated into a cellular endosome. Such an endosome may have a lower pH than other environments encountered by the nanocomposite (e.g. extracellular fluid, blood, saliva, cytoplasm, etc.). The acidic nature of the endosome may trigger release of the pharmaceutical compound from the nanocomposite. See, for example, Pindiprolu, et. al. [Pindiprolu, S. K. S. S., et. al., Medical Hypotheses, 2020, 143, 109858].

Method of Forming the Nanocomposite

The present disclosure also relates to a method of preparing the nanocomposite, the method comprising mixing an M source, an iron source, and the nanotubes of the silicate or aluminosilicate material in a first solvent to form a precursor mixture, adding a base to the precursor mixture to form a first reaction mixture, heating the reaction mixture to 75 to 105° C., preferably 80 to 100° C., preferably 82.5 to 97.5° C., preferably 85 to 95° C., preferably 87.5 to 92.5° C., preferably 89 to 91° C., preferably 90° C. to form a precipitate, isolating the precipitate to form a first product, calcining the first product to form the nanocarrier, mixing the nanocarrier and the pharmaceutical compound in a second solvent form a loaded nanocarrier, mixing the loaded nanocarrier and the biocompatible coating in a third solvent form a coated nanocarrier, and lyophilizing the coated nanocarrier to form the nanocomposite.

In some embodiments, the first solvent is water. In general, the M source may be any suitable salt of zinc, nickel, copper, manganese, or cobalt known to one of ordinary skill in the art. Preferably, the M source has a water solubility of at least 0.1 g/mL at room temperature. Examples of such suitable M sources include, but are not limited to acetate salts, halide salts including chloride, bromide and iodide salts and possibly including fluoride salts, nitrate salts, oxalate salts, sulfate salts, and combinations thereof. In preferred embodiments, the M source is an acetate salt and/or a nitrate salt. In some preferred embodiments, the M is zinc and the M source is zinc acetate. In alternative preferred embodiments, the M is nickel and the M source is nickel nitrate. In general, the iron source may be an iron salt of one of the above anions. In preferred embodiments, the iron source is iron nitrate.

In general, the base may be any suitable base known to one of ordinary skill in the art. Preferred bases include alkali metal hydroxides, particularly sodium hydroxide. In some embodiments, the base is present in the first reaction mixture in an amount of 0.001 to 0.015 g/mL, preferably 0.002 to 0.014 g/mL, preferably 0.003 to 0.013 g/mL, preferably 0.004 to 0.012 g/mL, preferably 0.005 to 0.011 g/mL, preferably 0.006 to 0.010 g/mL, preferably 0.007 to 0.009 g/mL, preferably 0.008 to 0.0085 g/mL.

In some embodiments, the calcining is performed at 250 to 750° C., preferably 275 to 725° C., preferably 300 to 700° C., preferably 325 to 675° C., preferably 350 to 650° C., preferably 375 to 625° C., preferably 400 to 600° C., preferably 425 to 575° C., preferably 450 to 550° C., preferably 475 to 525° C., preferably 490 to 510° C., preferably 500° C. In some embodiments, the calcining is performed for 1 to 10 hours, preferably 2 to 8 hours, preferably 3 to 7 hours, preferably 4 to 6 hours, preferably 5 hours.

In some embodiments, the method further comprises washing the precipitate. Such washing may be performed before calcining. Such washing may be performed with any suitable solvent known to one of ordinary skill in the art. Examples of such suitable solvents include, but are not limited to water, methanol, ethanol, acetone, tetrahydrofuran, diethyl ether, and 2-propanol.

In some embodiments, pharmaceutical compound is mixed with the nanocarrier in an amount of 1 to 10 wt %, preferably 1.5 to 9.5 wt %, preferably 2 to 9 wt %, preferably 2.5 to 8.5 wt %, preferably 3 to 8 wt %, preferably 3.5 to 7.5 wt %, preferably 4 to 7 wt %, preferably 4.25 to 6.5 wt %, preferably 4.5 to 6 wt %, preferably 4.75 to 5.5 wt %, preferably 5 wt %, based on a total weight of the nanocarrier.

In some embodiments, the second solvent comprises phosphate buffered saline and methanol. In such embodiments, the second solvent may have any suitable volumetric ratio of phosphate buffered saline to methanol, for example from 10:1 to 1:10, preferably 9:1 to 1:9, preferably 7.5:1 to 1:7.5, preferably 6:1 to 1:5, preferably 5:1 to 1:2.5, preferably 4:1 to 1:1, preferably 3:1 to 1.5:1, preferably 2:1.

In some embodiments, the nanocarrier and pharmaceutical compound are mixed at −78 to 60° C., preferably −50 to 50° C., preferably −40 to 40° C., preferably −30 to 30° C., preferably −25 to 25° C., preferably −20 to 20° C., preferably −15 to 15° C., preferably −10 to 10° C., preferably −5 to 5° C., preferably about 0° C. In some embodiments, the nanocarrier and pharmaceutical compound are mixed for 1 to 36 hours, preferably 2 to 30 hours, preferably 3 to 27 hours, preferably 4 to 24 hours, preferably 5 to 21 hours, preferably 6 to 18 hours, preferably 7 to 15 hours, preferably 8 to 12 hours.

In some embodiments, the loaded nanocarrier and biocompatible coating are mixed at −78 to 60° C., preferably −50 to 50° C., preferably −40 to 40° C., preferably −30 to 30° C., preferably −25 to 25° C., preferably −20 to 20° C., preferably −15 to 15° C., preferably −10 to 10° C., preferably −5 to 5° C., preferably about 0° C. In some embodiments, the mixing comprises an initial mixing performed at ambient temperature followed by a second mixing at −25 to 25° C., preferably −20 to 20° C., preferably −15 to 15° C., preferably −10 to 10° C., preferably −5 to 5° C., preferably about 0° C. In some embodiments, the nanocarrier and pharmaceutical compound are mixed for 12 to 36 hours, preferably 14 to 34 hours, preferably 16 to 32 hours, preferably 18 to 30 hours, preferably 20 to 28 hours, preferably 22 to 26 hours, preferably 24 hours. In some embodiments, said mixing is performed in an inert atmosphere. In some embodiments, the biocompatible coating is mixed with the loaded nanocarrier in a biocompatible coating: loaded nanocarrier weight ratio of 10:1 to 1:5, preferably 7.5:1 to 1:3, preferably 5:1 to 1:2.5, preferably 3:1 to 1:1, preferably 2.5:1 to 1.5:1, preferably 2:1.

In some embodiments, the silicate or aluminosilicate material is halloysite, as described above.

In some embodiments, the pharmaceutical compound is dexamethasone as described above.

In some embodiments, the biocompatible coating is polyethylene glycol as described above. In some embodiments, the third solvent is water.

Method of Treating a Pulmonary Infection

The present disclosure also relates to a method of treating a pulmonary infection, the method comprising administering by inhalation a pharmaceutical composition comprising the nanocomposite.

The term "subject" and "patient" are used interchangeably. As used herein, they refer to any subject for whom or which therapy, including with the pharmaceutical compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In some embodiments, the pulmonary infection causes, results in, or is associated with acidosis and/or sepsis. Such acidosis and/or sepsis may be systemic or may be localized to lung tissue or a portion thereof. The pulmonary infection itself may be associated with a specific infection microenvironment which has a low pH (e.g. below approximately 6.75). The low pH associated with the acidosis and/or sepsis may be advantageous for the method of the current invention by facilitating efficient release of the pharmaceutical compound from the nanocomposite.

The administration by inhalation may be achieved using any suitable method or apparatus known by one of ordinary skill in the art. Examples of such tools include, but are not limited to dry powder inhalers, meter-dosed inhalers, soft mist inhalers, and nebulizers. The nanocomposite may form part of a pharmaceutical composition which is intended to assist or facilitate delivery of the nanocomposite to a patient.

In some embodiments, the pharmaceutical composition may consist of only the nanocomposite of the invention.

In some embodiments which use dry powder inhalers, the formulation may comprise a physiologically acceptable pharmacologically-inert carrier. Such carrier may serve simply as bulking agent when it is desired to reduce the nanocomposite concentration in a powder which is being delivered to a patient or may serve to improve the dispersability of the powder within a powder dispersion device in order to provide more efficient and reproducible delivery of the active agent and to improve the handling characteristics of the nanocomposite (e.g., flowability and consistency) to facilitate manufacturing and powder filling.

The carrier may be any amorphous or crystalline physiologically acceptable inert material of animal or vegetal source or combination thereof. Preferred materials are crystalline sugars and for example monosaccharides such as glucose or arabinose, or disaccharides such as maltose, saccharose, dextrose or lactose. Polyalcohols such as mannitol, sorbitol, malitol, lactitol and α-lactose monohydrate may also be used. The pharmaceutical composition may also comprise one or more active ingredients, preferably another antibiotic for the treatment by inhalation of a bacterial infection or other suitable excipients such as flavoring and taste masking agents.

In some embodiments, the pharmaceutical composition is intended for delivery as an aerosol. Such a pharmaceutical composition may have the nanocomposite present as a suspension or dispersion in an aerosol solvent. Examples of commonly-used aerosol solvents include water and ethanol. In some embodiments, the pharmaceutical composition further comprises an excipient. Such excipients may be useful as antioxidants, preservatives, solubilization aids, emulsifiers, flavorings, chelating agents, cosolvents, humectants, buffering agents, pH adjusters, suspending aids, and tonicity adjusters. Examples of such excipients include, but are not limited to acetone sodium bisulfate, ammonia, ascorbic acid and salts thereof, benzalkonium chloride, cetylpyridinium chloride, chlorobutanol, citric acid and salts thereof, EDTA sodium, glycerin, glycine, hydrochloric acid, lecithin, lysine and lysine monohydride, magnesium stearate, menthol, methylparaben, nitric acid, oleic acid, polyethylene glycol, polysorbates, polyvinylpyrrolidone, propylene glycol, propylparaben, saccharin, sodium bisulfate, sodium chloride, sodium hydroxide, sodium metabifulfite, sodium sulfite, sorbitan trioleate (Span 85), thymol, and tromethamine.

In some embodiments, the pharmaceutical composition comprises a propellant. Propellants may be useful to develop proper pressure to expel the pharmaceutical composition in the form of vapor in the pharmaceutical composition of aerosols. A propellant is typically a chemical with a vapor pressure greater than atmospheric pressure at 40° C. (105° F.). The propellant provides the force that expels the pharmaceutical composition from a container and additionally is responsible for the delivery of the pharmaceutical composition in the proper form (e.g., spray, foam, semisolid). When the propellant is a liquefied gas or a mixture of liquefied gases, it can also serve as the solvent for the nanocomposite. Types of propellants commonly used in pharmaceutical aerosols include chlorofluorocarbons, fluorocarbons (trichloromonofluoromethane, dichlorodifluoromethane), hydrocarbons (propane, butane, isobutane), hydrochlorofluorocarbons and hydrofluorocarbons, and inert gases (nitrogen, $NO_2$, and $CO_2$).

In some embodiments, the pharmaceutical composition causes, results in, or is associated with a lowering of the pH of lung tissue, saliva, oral tissue, mucus, lung lining fluid, or other suitable tissue or fluid which may be encountered during inhalation. Such lowering of pH may be caused by one or more components of the pharmaceutical composition, for example lactose. See for example Tootla, et. al. [Tootla, R., et. al., Arch Oral Biol. 2004, 49, 4, 275-83]. The low pH caused by the pharmaceutical composition may be advantageous for the method of the current invention by facilitating efficient release of the pharmaceutical compound from the nanocomposite.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms “effective amount”, “therapeutically effective amount”, “pharmaceutically effective amount” or “sufficient amount” refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate “effective amount” may differ from one individual to another. An appropriate “effective amount” in any individual case may be determined using techniques, such as a dose escalation study.

In some embodiments, the pharmaceutical compound is dexamethasone and the nanocomposite is administered in an amount of 0.5 to 15 μg/mL, preferably 0.75 to 10 μg/mL, preferably 1.0 to 7.245 μg/mL, preferably 1.5 to 5 μg/mL, preferably 1.81 to 3.62 μg/mL of infected tissue. In some embodiments, the nanocomposite is administered in an amount of 0.5 to 15 μg/mL, preferably 0.75 to 10 μg/mL, preferably 1.0 to 7.245 g/mL, preferably 1.5 to 5 μg/mL, preferably 1.81 to 3.62 μg/mL of lung volume.

The treatment method may comprise administering the nanocomposite of the current disclosure as a single dose or multiple individual divided doses. In such embodiments, the nanocomposite may be accumulated and release the loaded pharmaceutical compound in or nearby diseased tissues. In some embodiments, the pharmaceutical composition is administered at various dosages (e.g. a first dose with an effective amount of nanocomposite comprising a first amount of the pharmaceutical compound per kilogram of the subject and a second dose with an effective amount of the nanocomposite comprising a second amount of the pharmaceutical compound per kilogram of the subject which is smaller than the first amount). In some embodiments, the interval of time between the administration of the nanocomposite and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. In some embodiments, the nanocomposite is administered once daily, twice daily, thrice daily, or four times daily for at least 2 days, 5 days, 6 days, or 7 days. In certain embodiments, the nanocomposite and one or more additional therapies are administered less than 1 day, 1 week, 2 weeks, 3 weeks, 4 weeks, 1 month, 2 months, 3 months, or 6 months apart. In some embodiments, the administration is stopped once the subject is treated (e.g. no longer showing signs or symptoms of infection).

The examples below are intended to further illustrate protocols for preparing and determining the properties of the nanocomposite and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

Synthesis Condition of Zincferrite/Halloysite Nanocarrier 1.01 g of $FeNO_3$ and 0.54 g of Zn acetate was dissolved in 60 ml water and stirred for 10 min. Then after dissolution, 1.4 g of Halloysite nanoclay was added and stirred for 30 min. Then 5 ml of a solution of 0.5 g NaOH in water was added and stirred for 10 min. Then, the temperature was increased to 90° C. and maintained for 2 h with stirring in a polypropylene bottle. Then, the mixture was cooled, filtered, the solid residue washed with water and dried at 80° C. overnight, then calcined at 500° C. for 5 h (5° C./min).

Synthesis Condition of Nickelferrite/Halloysite Nanocarrier 1.03 g of $FeNO_3$ and 0.74 g of nickel nitrate and dissolved in 60 ml water and stirred for 10 min. Then after dissolution, 1.4 g of Halloysite nanoclay was added and stirred for 30 min. Then 5 ml of a solution of 0.5 g NaOH in water was added and stirred for 10 min. Then, the temperature was increased to 90° C. and maintained for 2 h with stirring in a polypropylene bottle. Then, the mixture was cooled, filtered, the solid residue washed with water and dried at 80° C. overnight, then calcined at 500° C. for 5 h (5° C./min).

Functionalization With Dexamethasone 30 mg Dexamethasone was dissolved in 10 ml of methanol: PBS (pH 7.2) mixture (1:2) and stirred for 20 min. Next, 600 mg of Zincferrite/Halloysite or Nickelferrite/Halloysite nanocarrier was added and stirred overnight at ice cool condition. The resulting suspension was then filtered, the solid residue washed with 5 ml methanol PBS 7.2 solution and finally air dried.

Wrapping with biocompatible polymer Polyethylene glycol ($M_n$ 400)

10 ml of distilled water was mixed with 40 mg of PEG and 20 mg of Dexa/Zincferrite/Halloysite or Dexa/Nickelferrite/Halloysite and stirred for 10 min in an Argon inert atmosphere at ambient temperature, then cooled and stirred at ice cold for 24 h. Then the nanocomposite was freeze dried using lyophilization technique.

Characterization of Prepared Nanocomposites

FIG. 1 shows the PXRD patterns for prepared nanocarriers, nanocarrier loaded with dexamethasone, and the nanocomposites after coating with PEG. Zincferrite/Halloysite nanocomposite showed the presence of magnetic Zincferrite phase along with halloysite. Dexamethasone is reported to show crystalline peaks between 2 theta range 6.54° to 17.7°. After drug loading over Zincferrite/Halloysite and nickel ferrite/Halloysite, the drug showed a reduced intensity of reflections of dexamethasone, which shows partial transformation of drugs in nanoparticle forms. However, the presence of peaks of dexamethasone indicates some presence of crystalline nature of drug preserved in conjugation with the nanotubes of halloysite. The peaks of dexamethasone showed a slight intensity reduction after wrapping with PEG over nanocomposite.

Figure 2:
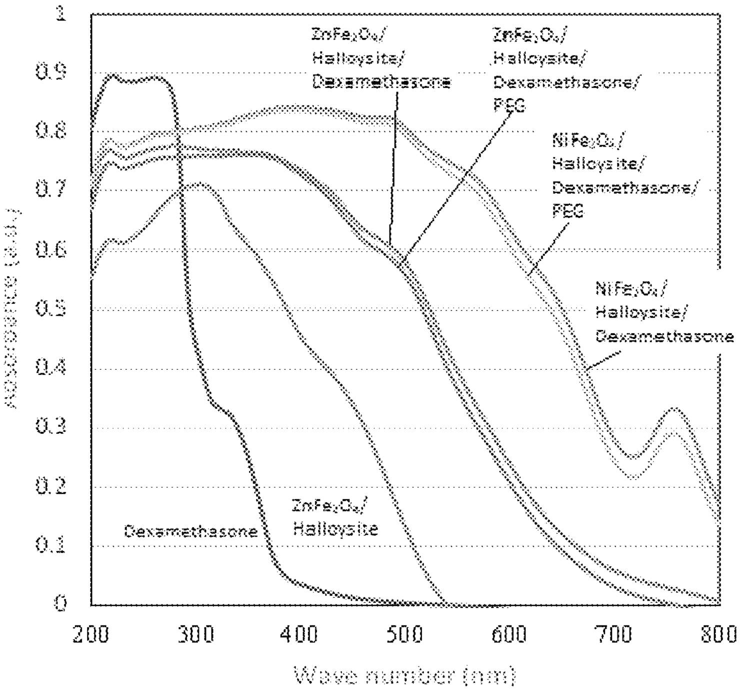
FIG. 2 shows Diffuse reflectance spectra of dexamethasone, and of various nanocomposites of the current invention including Zinc ferrite/Halloysite, Zinc ferrite/Halloysite/Dexamethasone, Zinc ferrite/Halloysite/Dexamethasone/PEG, Nickel ferrite/Halloysite/Dexamethasone, and Nickel ferrite/Halloysite/Dexamethasone/PEG.

FIG. 2 shows the solid spectra of Dexamethasone, Zinc ferrite/Halloysite, Zinc ferrite/Halloysite/Dexamethasone, Zinc ferrite/Halloysite/Dexamethasone/PEG, Nickel ferrite/Halloysite/Dexamethasone, and Nickel ferrite/Halloysite/Dexamethasone/PEG. In case of Zinc ferrite/Halloysite, a unique absorption occurs at lower absorption range of 210 nm and 300 nm due to presence of $Zn^{2+}$ species and $Fe_2O_4$ species. The nanotube halloysite peaks can be observed between 400-500 nm. Dex showed a strong absorption at about 200-300 nm and addition peak appears at about 350 nm. An enhancement in peak absorption occurs over Zinc ferrite/Halloysite/Dexamethasone and Nickel ferrite/Halloysite/Dexamethasone nanocomposites. This clearly indicates the influence of dexamethasone functionalization over halloysite.

Figure 3A:
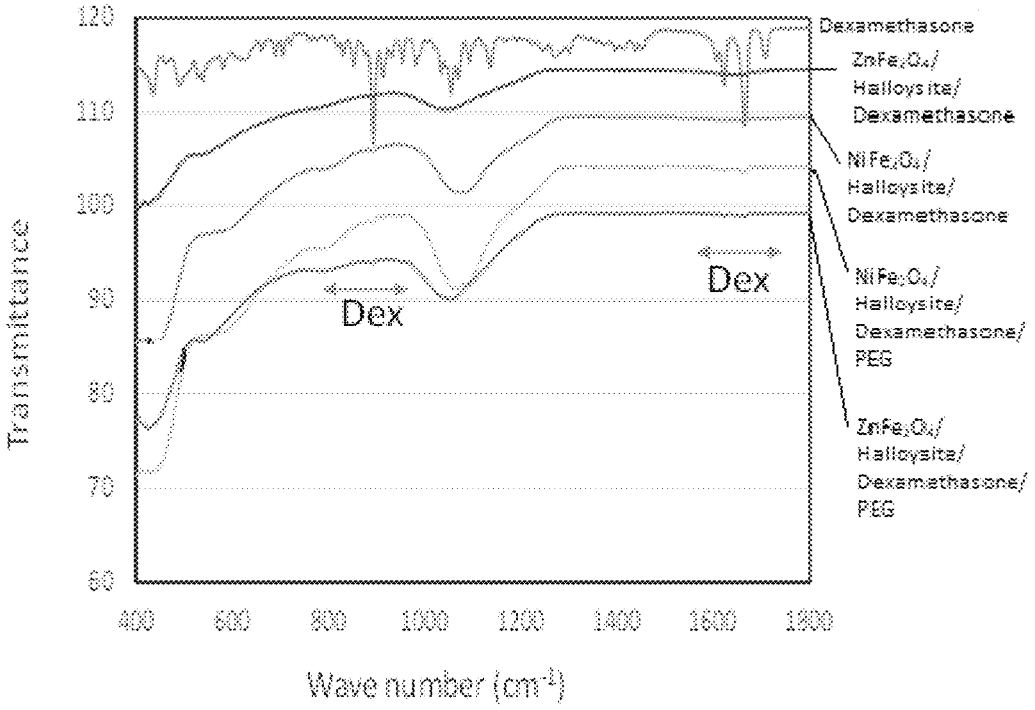
FIGS. 3A-3B are FTIR spectra of various nanocomposites of the current invention where
Figure 3B:
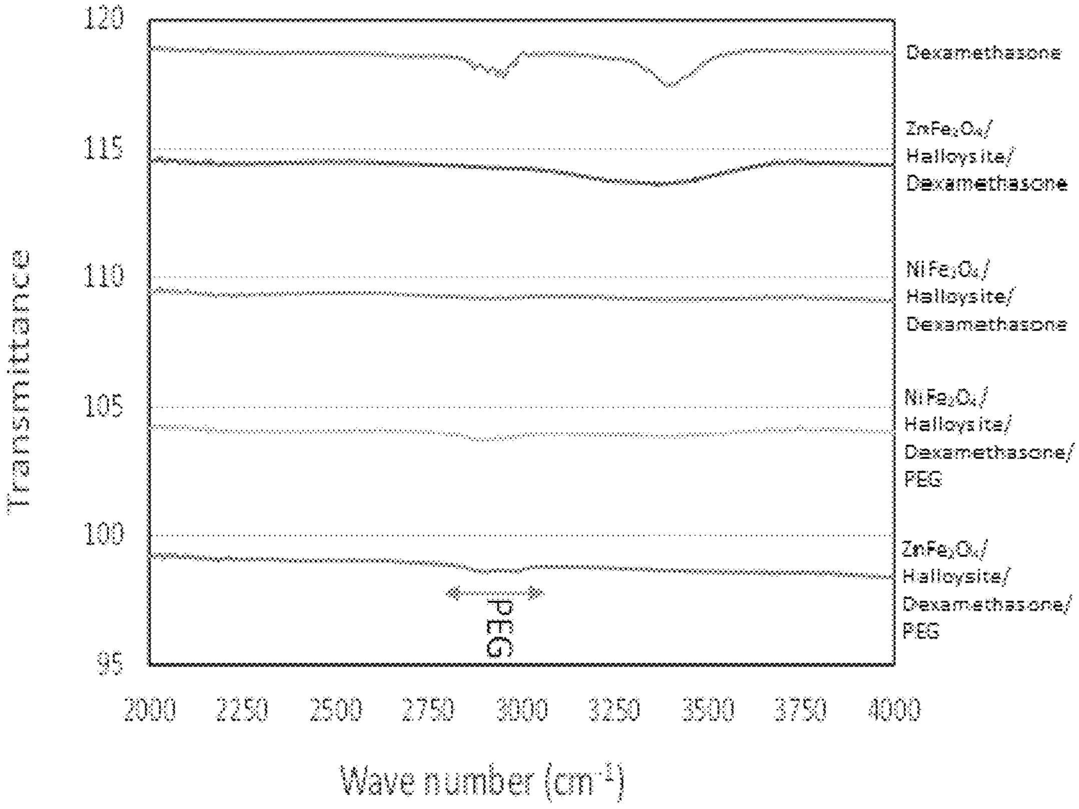
Figure 4A:
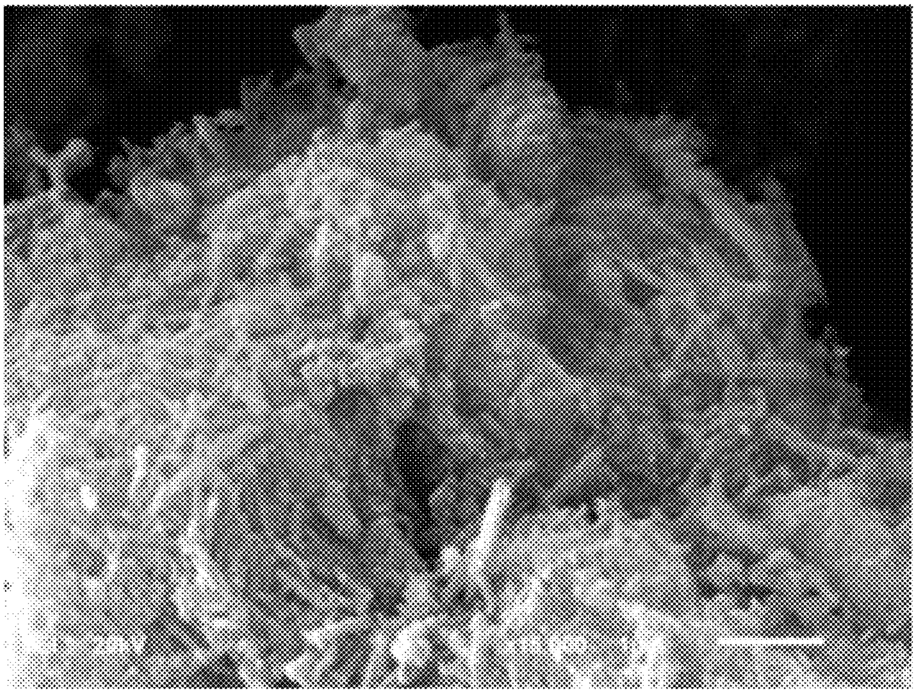
FIGS. 4A-4C are SEM images showing an exemplary $ZnFe_2O_4$/Halloysite nanocarrier.
Figure 4B:
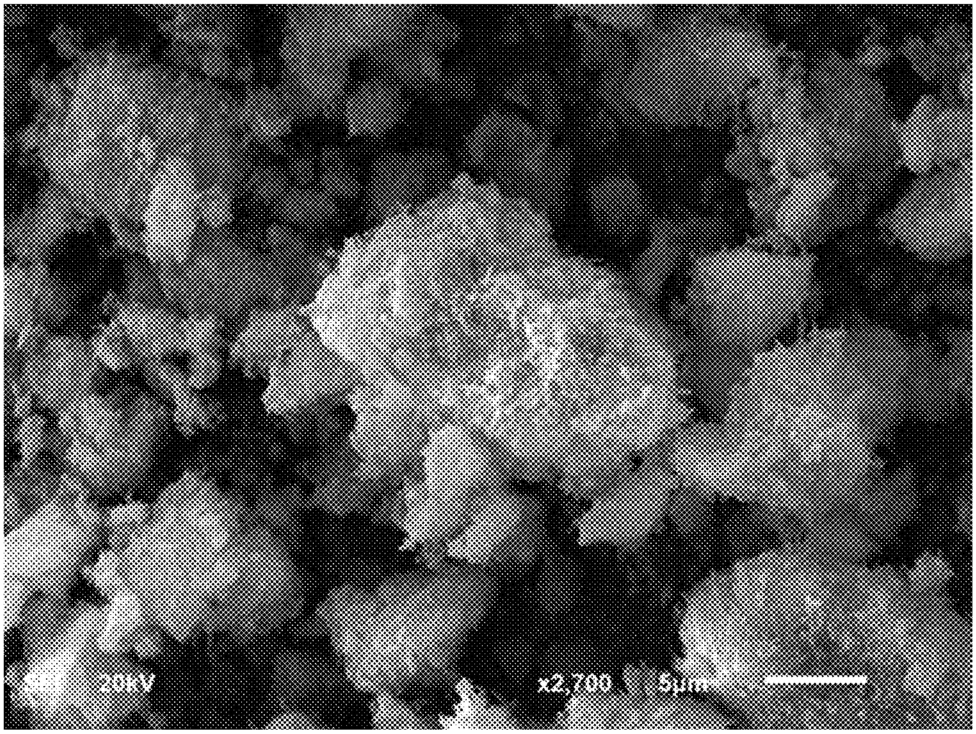
Figure 4C:
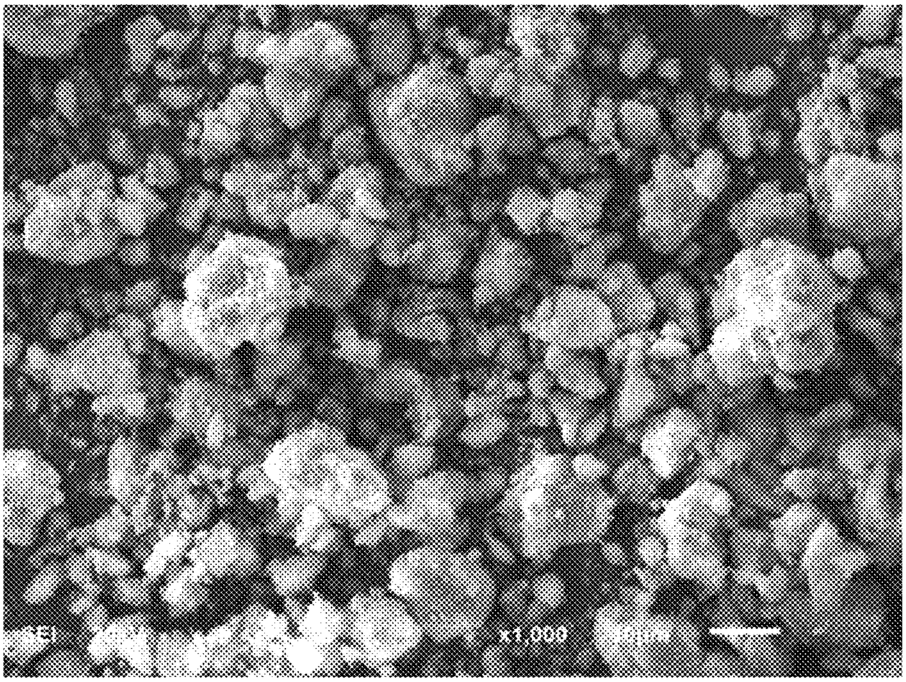
Figure 5A:
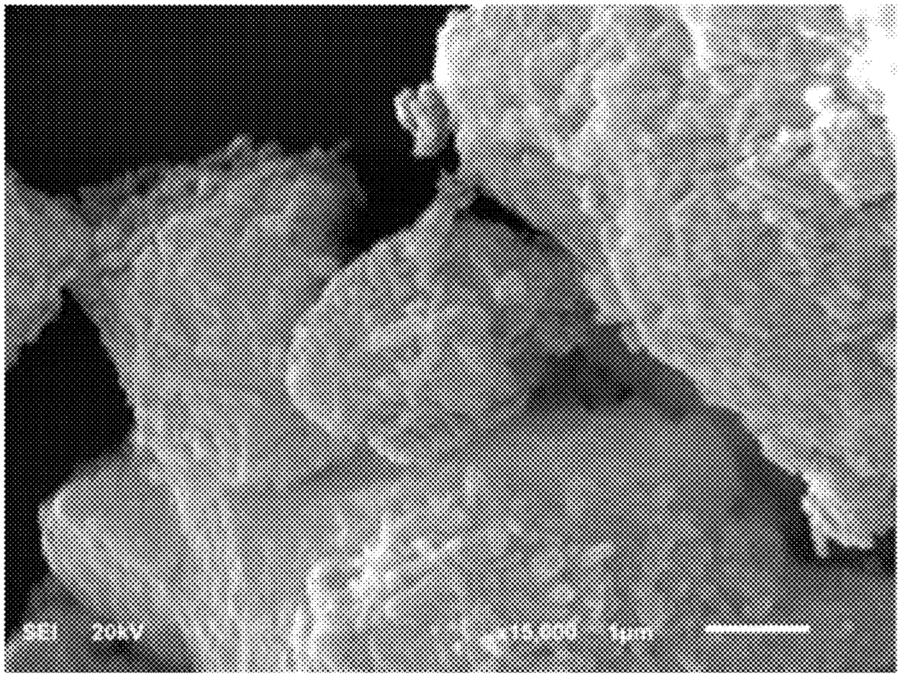
FIGS. 5A-5C are SEM images showing an exemplary $ZnFe_2O_4$/Halloysite/PEG nanocomposite.
Figure 5B:
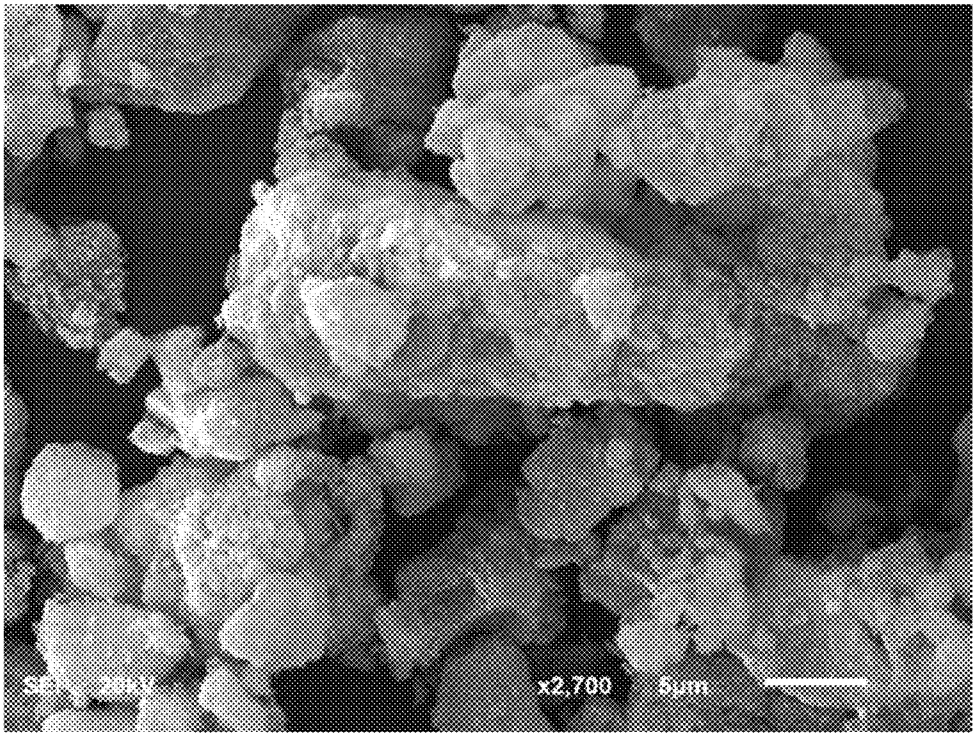
Figure 5C:
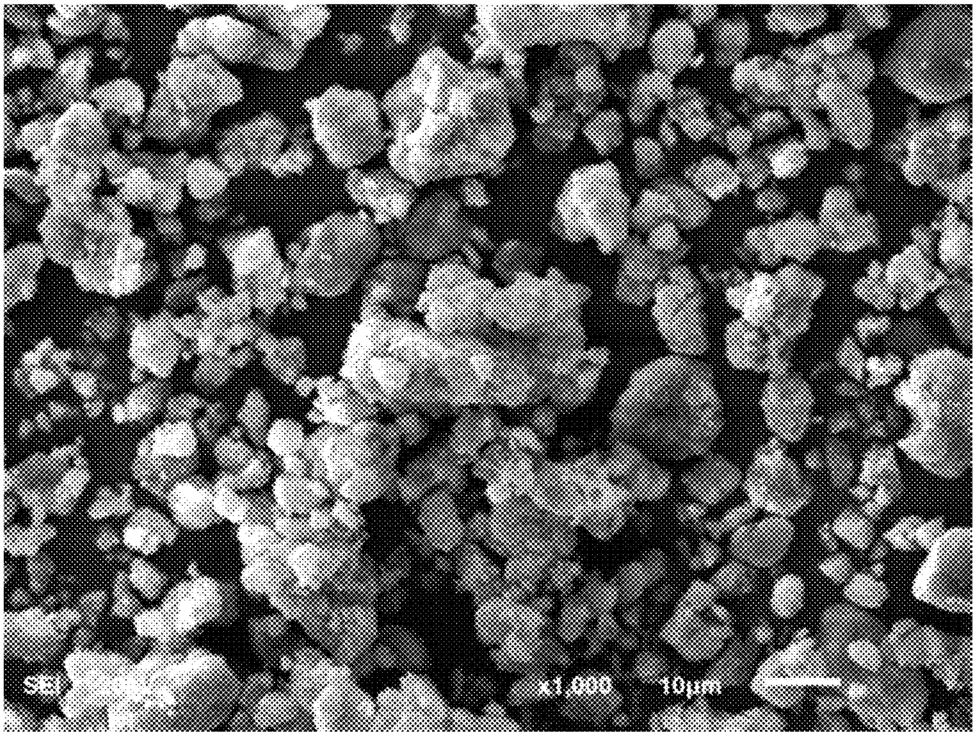
Figure 6A:
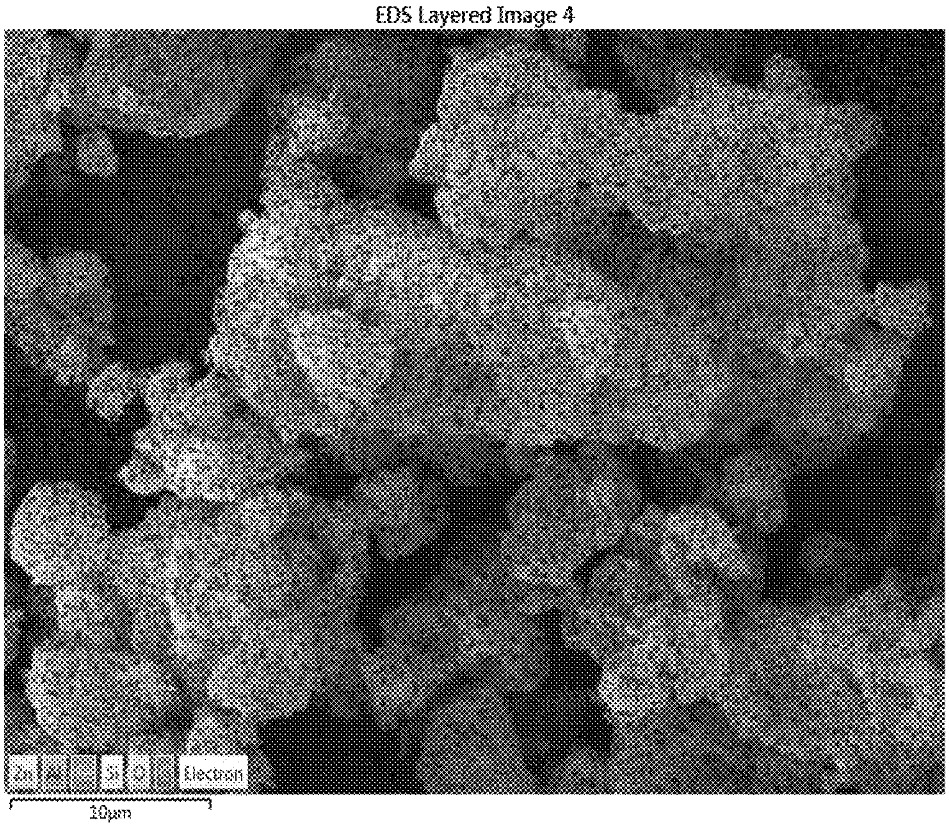
FIGS. 6A-6H are EDS results showing the elemental distribution and makeup of an exemplary $ZnFe_2O_4$/Halloysite/PEG nanocomposite where
Figure 6B:
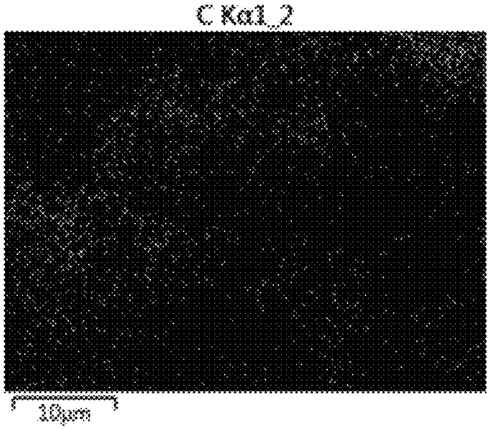
Figure 6C:
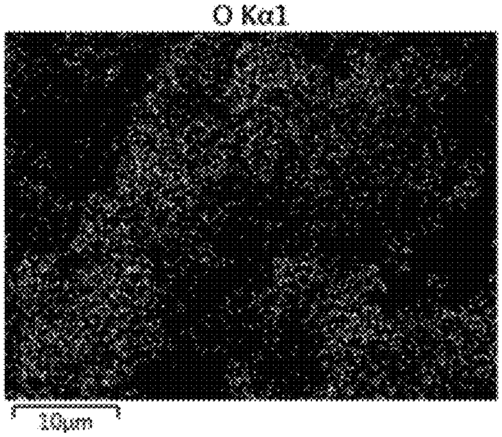
Figure 6D:
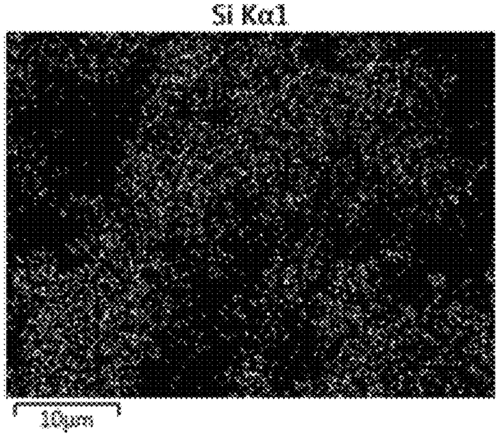
Figure 6E:
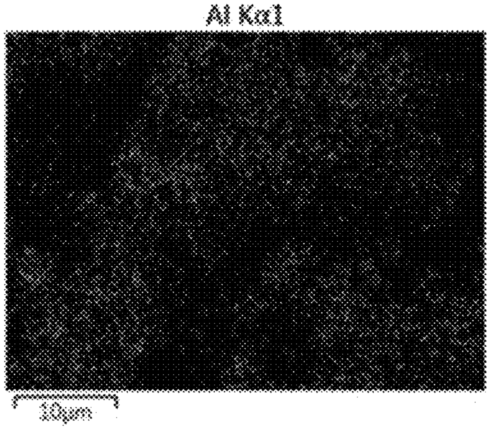
Figure 6F:
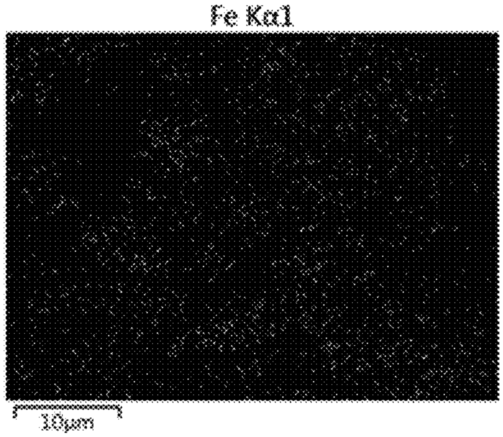
Figure 6G:
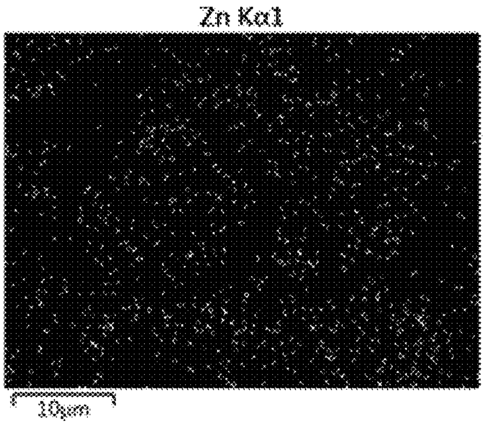
Figure 6H:
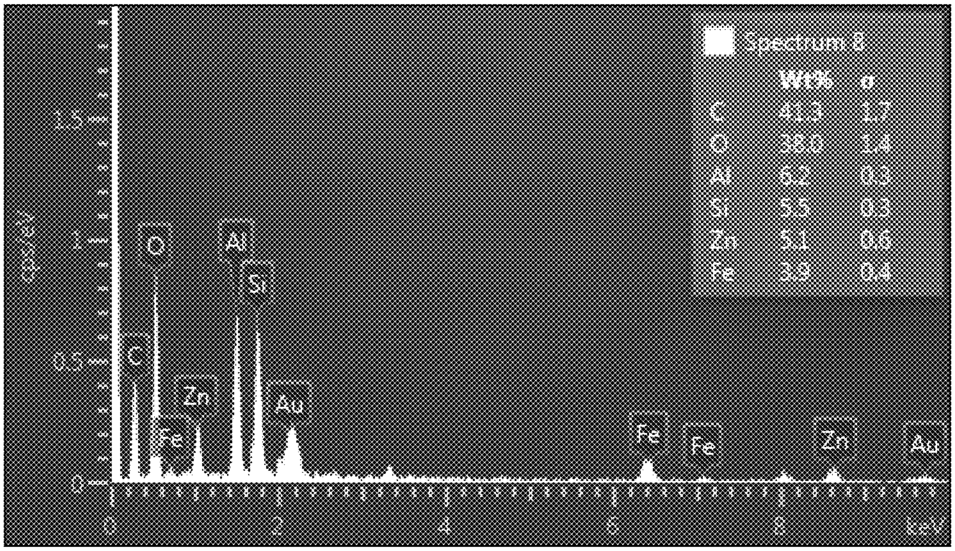
Figure 7A:
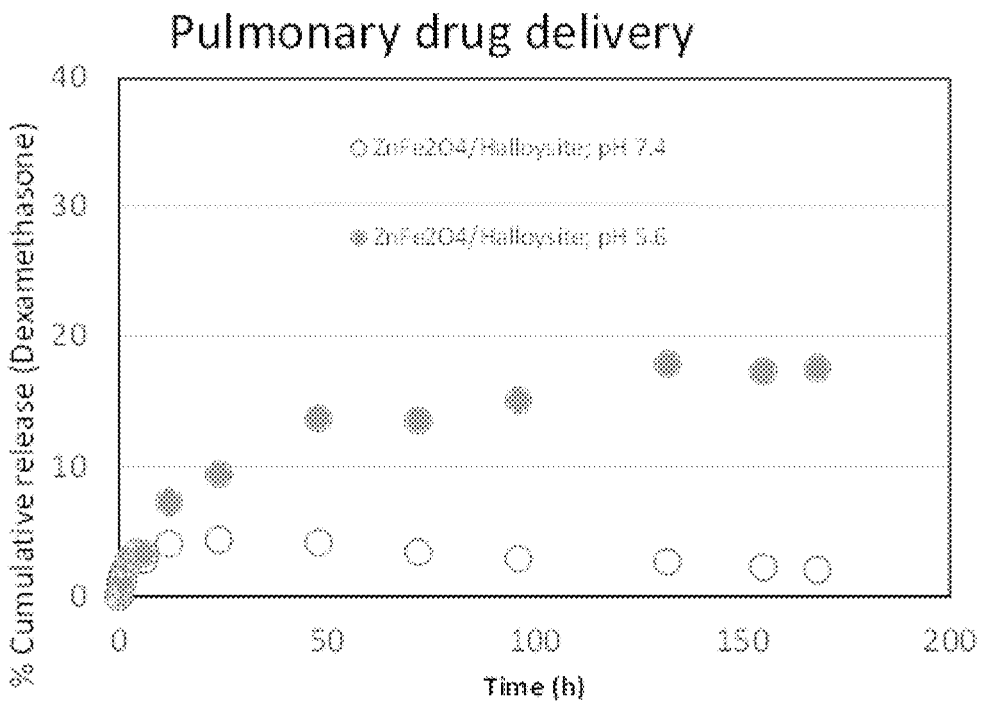
FIGS. 7A-7C show plots of the cumulative dexamethasone release from various synthesized nanocomposites at pH 7.4 and pH 5.6 where
Figure 7B:
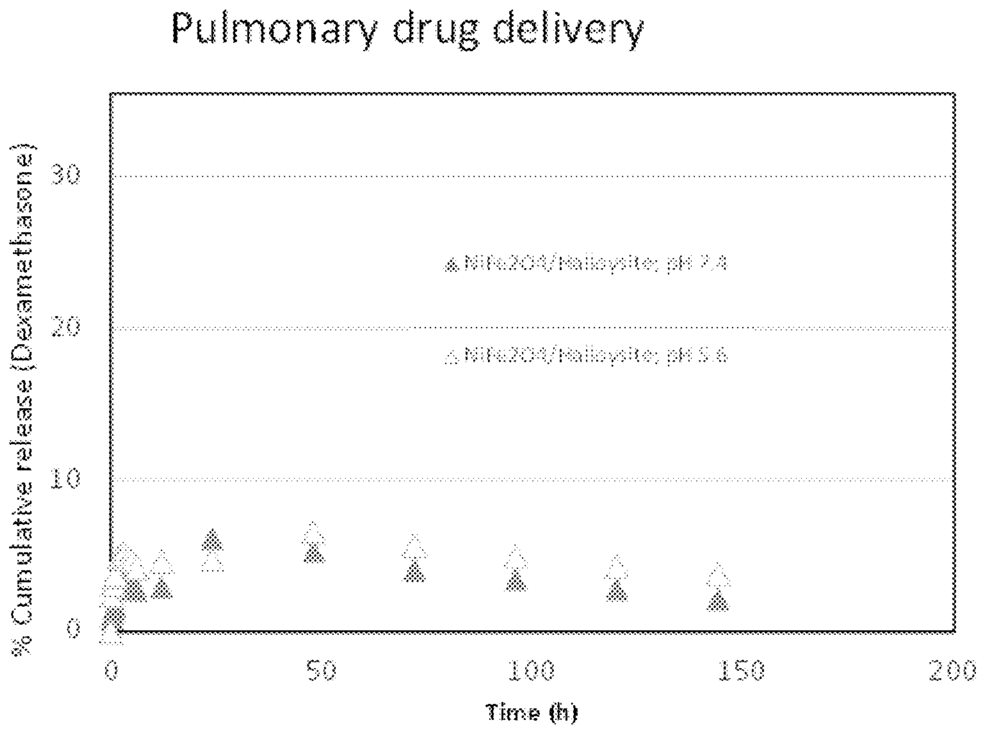
Figure 7C:
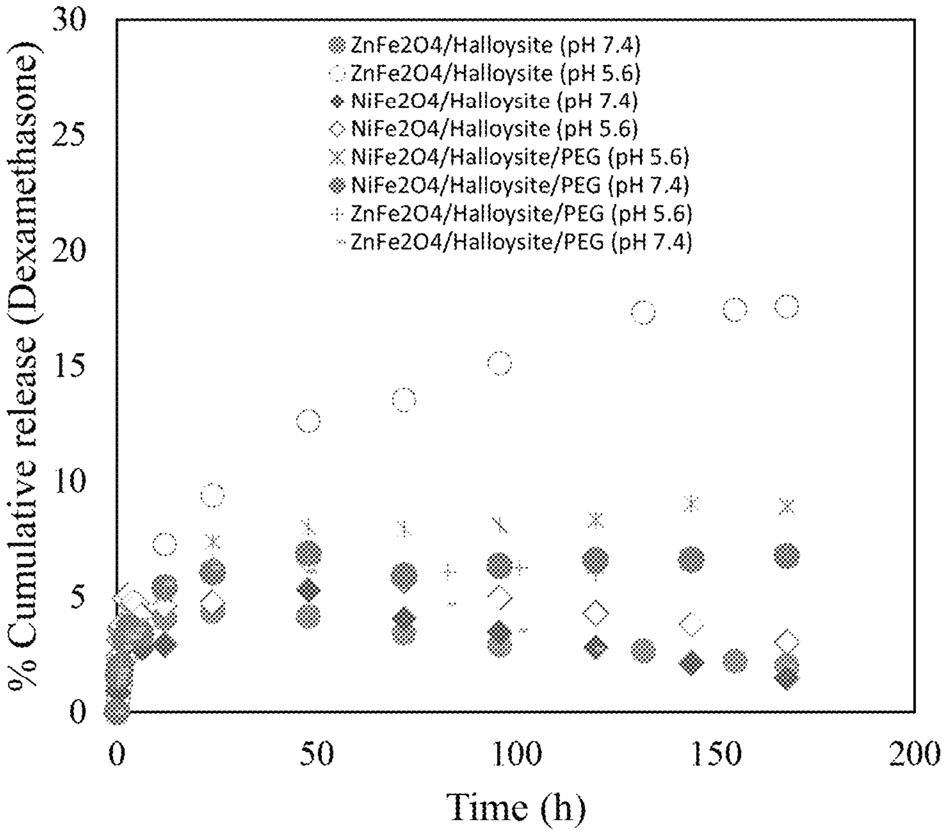

FIGS. 3A-3B show the FTIR spectra of both dexamethasone and various ferrite/Halloysite composites. The FTIR spectra of Dexamethasone showed several peaks stretching between 4000-400 $cm^{-1}$. On functionalization over ferrite/Halloysite, the characteristic peaks of dexamethasone disappear while some reduced peak stretching indicates that effective coordination of dexamethasone with zinc ferrite/halloysite and nickel ferrite/halloysite nanocarriers. The reduction in peaks indicates the incorporation of drugs inside the pore channels, while the presence of PEG was identified with characteristics peaks of hydroxyl groups at about 2800-3000 $cm^{-1}$.

The release of dexamethasone found to depend on the pH conditions. At neutral pH 7.4, less dexamethasone was found to be released (<5%). It is worth noting that at pH 5.6, controlled release of dexamethasone occurs and also the release is in sustained manner (<20%). This shows the excellent stimuli responsive drug delivery pattern.

The release of dexamethasone over Nickelferrite/Halloysite was not found to depend on the pH conditions. At both pH conditions, dexamethasone release less than 10% was found to be released.

Figure 8A:
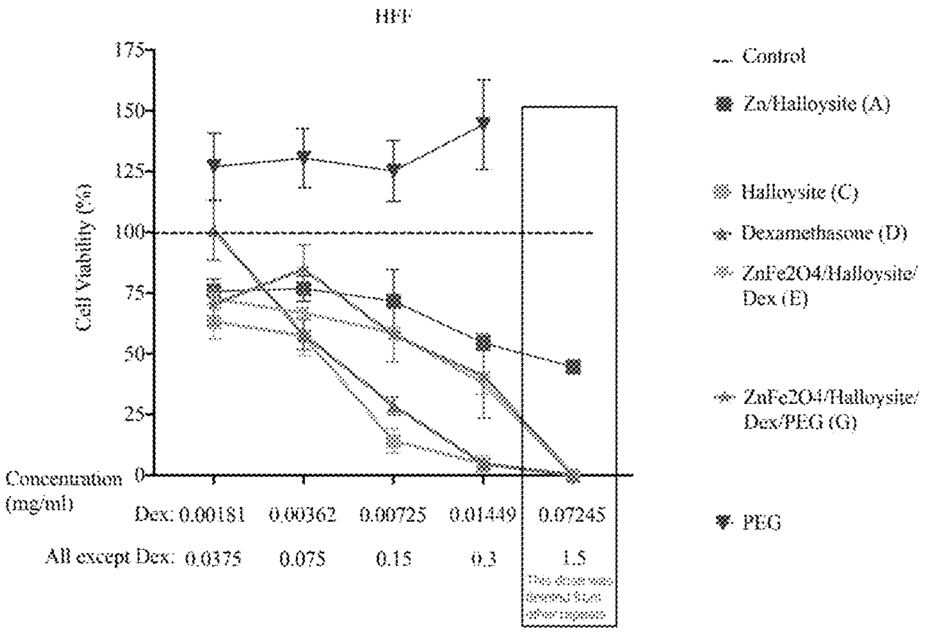
FIGS. 8A-8B are plots of cell viability of human foreskin fibroblasts (HFF) vs dose for dexamethasone and various nanocomposites of the current invention, where
Figure 8B:
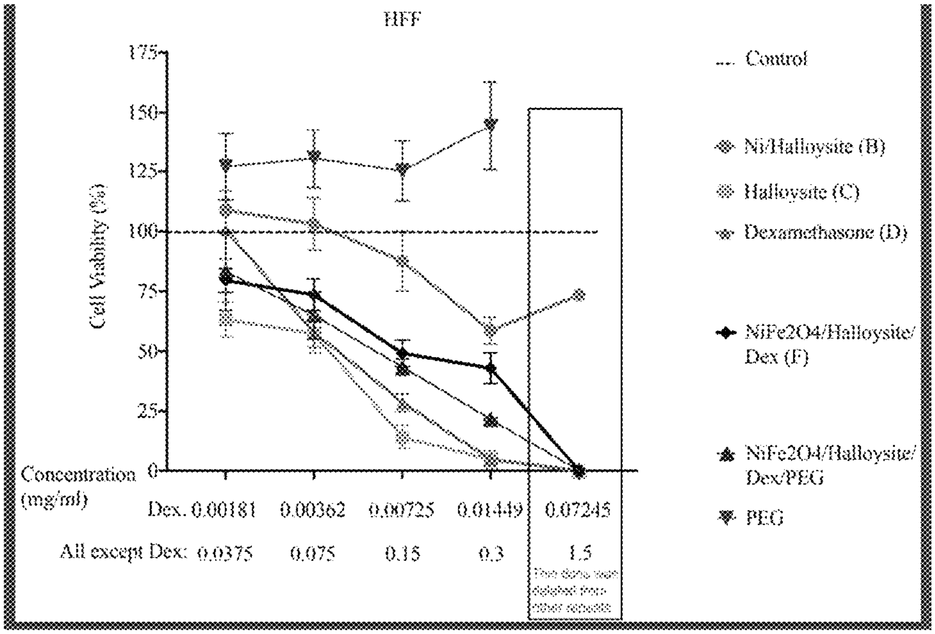
Figure 9A:
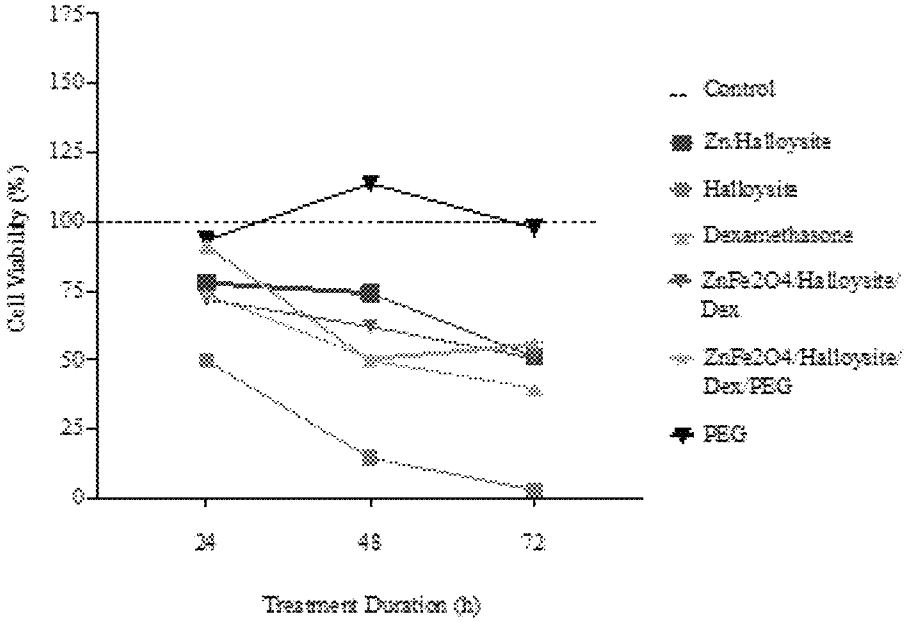
FIGS. 9A-9C are plots of cell viability of HFF cells treated with the stated conditions for 24, 48, and 72 h, where
Figure 9B:
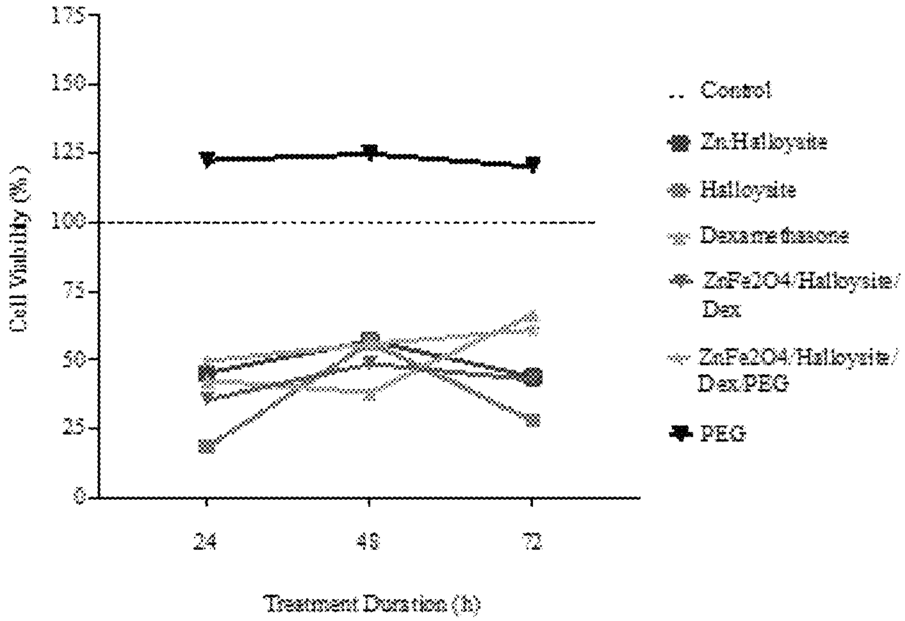
Figure 9C:
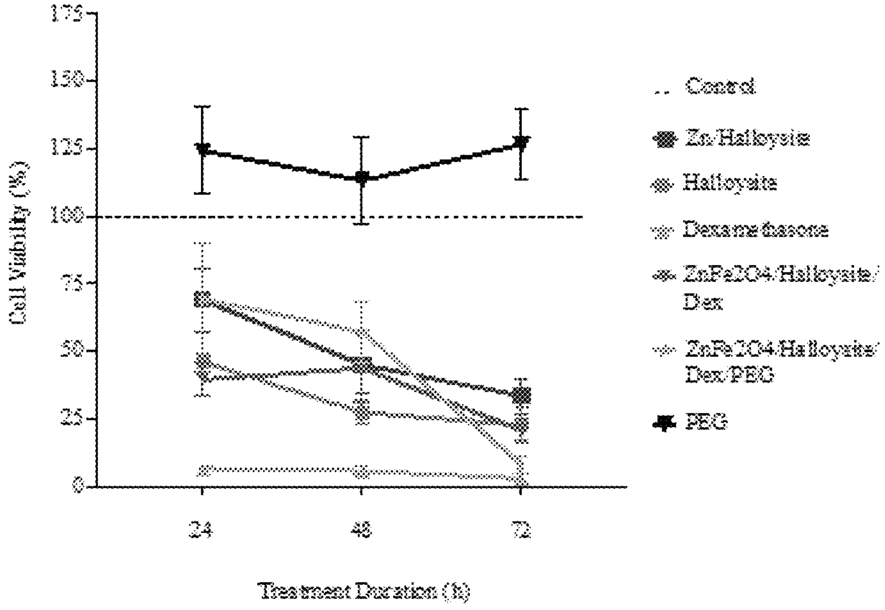
Figure 10:
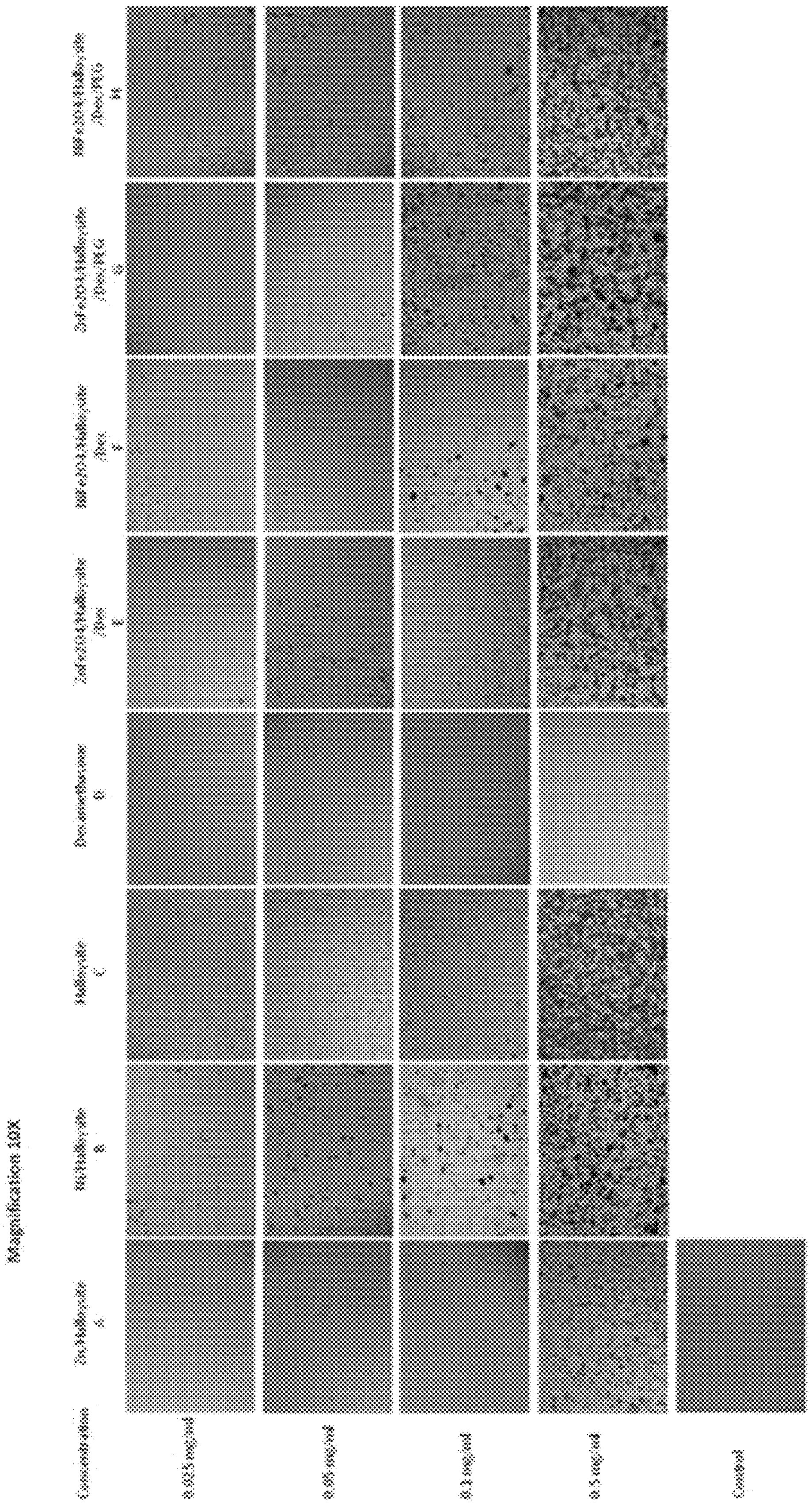
FIG. 10 shows light microscopy images of HFF cells treated with various nanocomposites.
Figure 11:
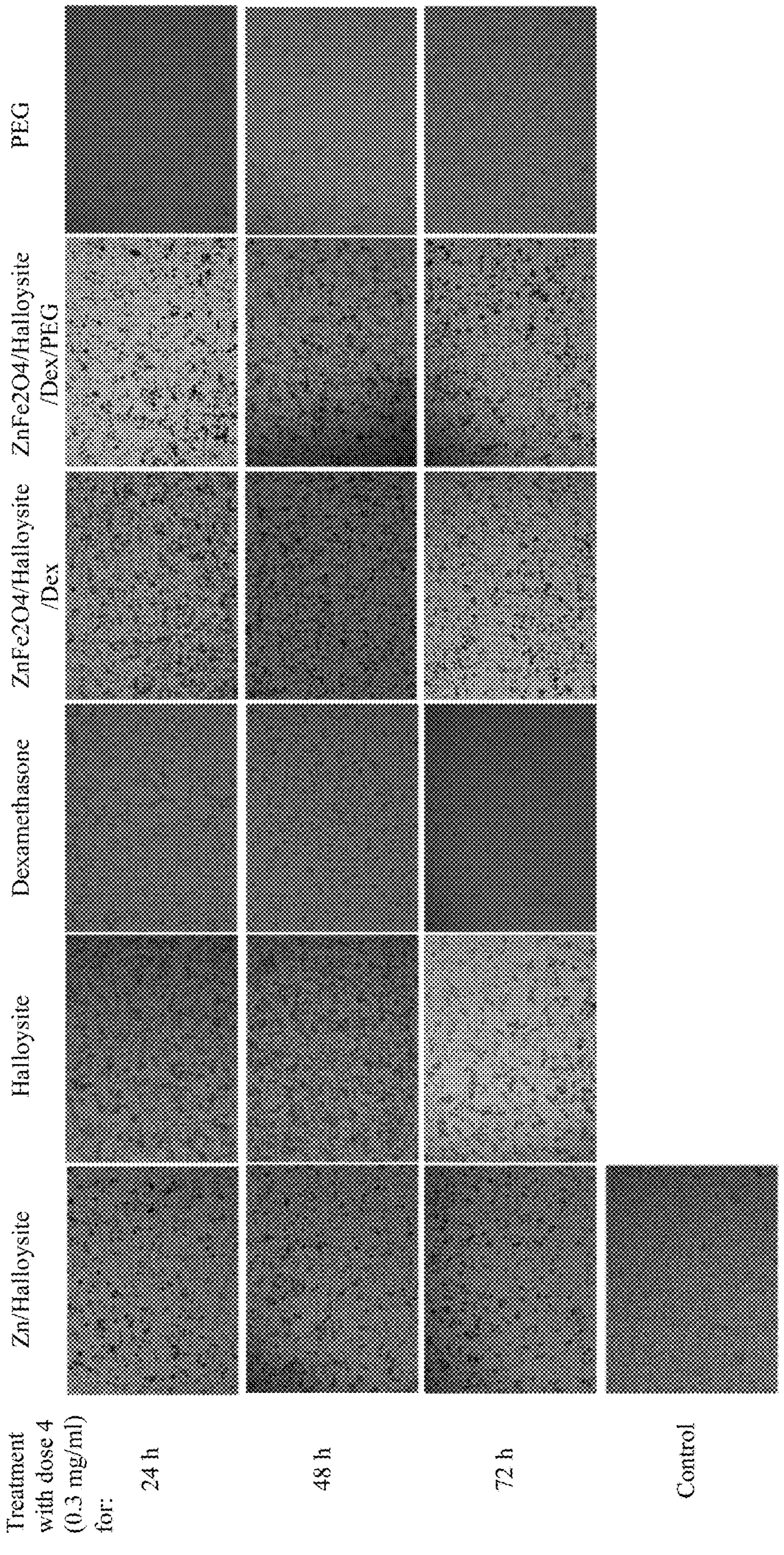
FIG. 11 shows light microscopy images of HFF cells treated with various nanocomposites at 0.3 mg/mL for 24 h, 48 h, and 72 h.

Toxicity studies were carried out to evaluate any toxic effect of developed nanoformulations. Cells were treated for 48 h with the following conditions for Zinc-containing nanocomposites: $ZnFe_2O_4$/Halloysite, Halloysite, Dexamethasone (Dex), $ZnFe_2O_4$/Halloysite/Dex, $ZnFe_2O_4$/Halloysite/Dex/PEG, and PEG. Similar protocol was used for nickel-containing nanocomposites. Treatment concentrations were as follows: 0.0375, 0.075, 0.15, and 0.3 mg/mL. In addition, cells were treated with Dex at concentrations to reflect that loaded in the nanocomposite as follows: 0.00181, 0.00362, 0.00725, and 0.01449 mg/mL. The results of these studies are presented in FIGS. 8A-8B and FIGS. 9A-9C. FIGS. 8A-8B show the toxicity profile of pure dexamethasone, halloysite and developed nanoformulation in HFF normal cells (Human foreskin fibroblasts). The dexamethasone dose up to 0.00362 mg/mL was found to be less toxic and are recommended for present nanoformulation. Both halloysite and dexamethasone was found to induce toxicity to cells but nanocomposite formation with biocompatible zinc ferrite and polyethylene glycol reduces the toxicity and can be used in the dose up to 0.00362 mg/mL. To choose the optimal dose, cells were exposed to specific doses at different time points. Cells were treated with dose 2 (0.075 mg/mL, see FIG. 9A), dose 3 (0.15 mg/mL, see FIG. 9B), or dose 4 (0.3 mg/mL, see FIG. 9C) for 24, 48, and 72 h. Upon analysis of these results, dose 4 was chosen as the optimal dose as it shows a distinct separation between the cell viability curves. This was confirmed with statistical analysis of dose 4 treatment for 24, 48, and 72 h (see Tables 1-3) and the morphological assessment of treated cells (see FIGS. 10-11). This analysis shows that when comparing the nanocomposites with Dex, there is a statistically significant improvement in cell viability of HFF cells at 24 and 48 h. These results suggest that the nanocomposites are able to prevent the toxic effects of Dex while in blood circulation until it reaches the target tissue.

TABLE 1

Statistical analysis for each group compared with either the control (no treatment) or Dexamethasone treated for 24 h.

| | Comparison | | | |
|---|---|---|---|---|
| | Control | | Dexamethasone | |
| Treatment Group | Significant | P value | Significant? | P value |
| PEG | No | 0.0920 | Yes | <0.0001 |
| Zn + Halloysite | Yes | 0.0226 | Yes | <0.0001 |
| Halloysite | Yes | <0.0001 | Yes | 0.0030 |
| Dexamethasone | Yes | <0.0001 | — | — |
| $ZnFe_2O_4$ + Halloysite + Dex | Yes | <0.0001 | Yes | 0.0145 |
| $ZnFe_2O_4$ + Halloysite + Dex + PEG | Yes | 0.0248 | Yes | <0.0001 |

TABLE 2

Statistical analysis for each group compared with either the control (no treatment) or Dexamethasone treated for 48 h.

| | Comparison | | | |
|---|---|---|---|---|
| | Control | | Dexamethasone | |
| Treatment Group | Significant | P value | Significant? | P value |
| PEG | No | 0.5931 | Yes | <0.0001 |
| Zn + Halloysite | Yes | <0.0001 | Yes | 0.0030 |
| Halloysite | Yes | <0.0001 | No | 0.1628 |
| Dexamethasone | Yes | <0.0001 | — | — |
| $ZnFe_2O_4$ + Halloysite + Dex | Yes | <0.0001 | Yes | 0.0041 |
| $ZnFe_2O_4$ + Halloysite + Dex + PEG | Yes | 0.0012 | Yes | 0.0002 |

TABLE 3

Statistical analysis for each group compared with either the control (no treatment) or Dexamethasone treated for 72 h.

| | Comparison | | | |
|---|---|---|---|---|
| | Control | | Dexamethasone | |
| Treatment Group | Significant | P value | Significant? | P value |
| PEG | No | 0.0.0573 | Yes | <0.0001 |
| Zn + Halloysite | Yes | <0.0001 | Yes | 0.0243 |
| Halloysite | Yes | <0.0001 | No | 0.2231 |
| Dexamethasone | Yes | <0.0001 | — | — |
| $ZnFe_2O_4$ + Halloysite + Dex | Yes | <0.0001 | No | 0.3118 |
| $ZnFe_2O_4$ + Halloysite + Dex + PEG | Yes | <0.0001 | No | 0.9894 |

The invention claimed is:

1. A magnetic ferritic nanocomposite, comprising:

a nanocarrier comprising:

nanotubes of halloysite, and nanoparticles of a magnetic transition metal ferrite material of formula $MFe_2O_4$, where M is selected from the group consisting of zinc and nickel, the nanoparticles being disposed on an interior and/or an exterior surface of the nanotubes;

a pharmaceutical compound disposed on a surface of the nanocarrier; and a biocompatible coating disposed on the pharmaceutical compound, wherein the nanocarrier has a surface area of 50 to 100 $m^2/g$, a pore volume of 0.2 to 0.4 $cm^3/g$, and a mean pore size of 10 to 20 nm; and the biocompatible coating comprises polyethylene glycol having a number average molecular weight of 350 to 450 g/mol.

2. The nanocomposite of claim 1, wherein the nanotubes have an exterior surface which is negatively charged and an interior surface which is positively charged.

3. The nanocomposite of claim 1, wherein the nanotubes have a mean nanotube outer diameter of 10 to 125 nm and a mean nanotube length of 0.25 to 7.5 μm.

4. The nanocomposite of claim 1, wherein the nanoparticles have a mean particle size of 1 to 100 nm.

5. The nanocomposite of claim 1, wherein the nanoparticles are present in an amount of 1 to 50 wt %, based on a total weight of the nanocarrier.

6. The nanocomposite of claim 1, wherein the pharmaceutical compound is dexamethasone.

7. The nanocomposite of claim 1, wherein the pharmaceutical compound is present in an amount of 1 to 10 wt % based on a total weight of the nanocomposite.

8. The nanocomposite of claim 1, further comprising a targeting agent disposed on the surface of the nanocarrier and/or on the biocompatible coating.

9. The nanocomposite of claim 1, wherein the nanocomposite releases 1 to 30 mol % of the pharmaceutical compound after 50 to 250 hours at a pH of 4.5 to 7, based on an initial amount of pharmaceutical compound present in the nanocomposite.

10. A method of preparing the nanocomposite of claim 1, the method comprising:

mixing an M source, an iron source, and the nanotubes of halloysite in a first solvent to form a precursor mixture, adding a base to the precursor mixture to form a first reaction mixture, heating the reaction mixture to 75 to 105° C. to form a precipitate, isolating the precipitate to form a first product, calcining the first product to form the nanocarrier;

mixing the nanocarrier and the pharmaceutical compound in a second solvent to form a loaded nanocarrier;

mixing the loaded nanocarrier and polyethylene glycol having a number average molecular weight of 350 to 450 g/mol in a third solvent to form a coated nanocarrier; and lyophilizing the coated nanocarrier to form the nanocomposite.

11. The method of claim 10, wherein the pharmaceutical compound is dexamethasone and the second solvent comprises phosphate buffered saline and methanol.

12. The method of claim 10, wherein the third solvent is water.

13. A method of treating a pulmonary infection, the method comprising administering by inhalation a pharmaceutical composition comprising the nanocomposite of claim 1.

14. The method of claim 13, wherein the pharmaceutical compound is dexamethasone and the nanocomposite is administered in an amount of 0.5 to 15 μg/mL of infected tissue.

* * * * *